United States Patent
Hirai et al.

(10) Patent No.: US 12,364,877 B2
(45) Date of Patent: Jul. 22, 2025

(54) MEDICAL IMAGE PROCESSING DEVICE, STORAGE MEDIUM, MEDICAL DEVICE, AND TREATMENT SYSTEM

(71) Applicants: Toshiba Energy Systems & Solutions Corporation, Kawasaki (JP); National Institutes for Quantum Science and Technology, Chiba (JP)

(72) Inventors: Ryusuke Hirai, Tokyo (JP); Yukinobu Sakata, Kawasaki Kanagawa (JP); Akiyuki Tanizawa, Kawasaki Kanagawa (JP); Keiko Okaya, Tokyo (JP); Shinichiro Mori, Chiba (JP)

(73) Assignees: Toshiba Energy Systems & Solutions Corporation, Kawasaki (JP); National Institutes for Quantum Science and Technology, Chiba (JP)

( * ) Notice: Subject to any disclaimer, the term of this patent is extended or adjusted under 35 U.S.C. 154(b) by 630 days.

(21) Appl. No.: 17/453,899

(22) Filed: Nov. 8, 2021

(65) Prior Publication Data

US 2022/0054862 A1     Feb. 24, 2022

Related U.S. Application Data

(63) Continuation of application No. PCT/JP2020/018234, filed on Apr. 30, 2020.

(30) Foreign Application Priority Data

May 14, 2019 (JP) .................. 2019-091410

(51) Int. Cl.
*A61N 5/10* (2006.01)
*G06T 11/00* (2006.01)

(52) U.S. Cl.
CPC .......... *A61N 5/1049* (2013.01); *G06T 11/006* (2013.01); *G06T 11/008* (2013.01); *A61N 2005/1062* (2013.01); *G06T 2210/41* (2013.01)

(58) Field of Classification Search
CPC ..................................................... G06T 11/008
See application file for complete search history.

(56) References Cited

U.S. PATENT DOCUMENTS

2010/0246915 A1   9/2010   Yamakoshi et al.
2013/0188856 A1   7/2013   Adler, Jr. et al.
(Continued)

FOREIGN PATENT DOCUMENTS

CN   104337536 A   2/2015
CN   108024779 A   5/2018
(Continued)

OTHER PUBLICATIONS

Combined Chinese Office Action and Search Report mailed Jun. 5, 2024 in corresponding Chinese Patent Application No. 202080034833.3 (with English translation), 8 pages.

*Primary Examiner* — Jeffrey G Hoekstra
*Assistant Examiner* — Gabriel Victor Popescu
(74) *Attorney, Agent, or Firm* — Oblon, McClelland, Maier & Neustadt, L.L.P.

(57) ABSTRACT

A medical image processing device of an embodiment includes first and second image acquirers, a generator, and a calculator. The first image acquirer acquires a first fluoroscopic image of a patient. The second image acquirer acquires a second fluoroscopic image according to radiation of the patient at a time point different from that of acquisition of the first image using a detector. The generator generates a reconstructed image by reproducing the second image from the first image virtually arranged in a three-dimensional space on the basis of a position of the detector in the three-dimensional space. The calculator obtains a (Continued)

suitable position on the first image in the three-dimensional space on the basis of a degree of similarity between the second image and the reconstructed image. The generator generates the reconstructed image for use in the calculator and has a range larger than a range corresponding to the second image.

11 Claims, 7 Drawing Sheets

(56) References Cited

U.S. PATENT DOCUMENTS

| | | | |
|---|---|---|---|
| 2014/0132597 A1 | 5/2014 | Tsukagoshi et al. | |
| 2015/0287189 A1 | 10/2015 | Hirai et al. | |
| 2016/0302747 A1* | 10/2016 | Averbuch | A61B 34/20 |
| 2017/0084025 A1* | 3/2017 | Lyu | G06T 7/70 |
| 2017/0209111 A1* | 7/2017 | Choi | A61B 6/032 |
| 2017/0291042 A1 | 10/2017 | Takahashi | |
| 2018/0315188 A1 | 11/2018 | Tegzes et al. | |
| 2019/0175941 A1* | 6/2019 | Miyazaki | A61B 6/5217 |

FOREIGN PATENT DOCUMENTS

| | | |
|---|---|---|
| JP | 2013-39360 A | 2/2013 |
| JP | 2017-189285 A | 10/2017 |

* cited by examiner

X-RAY FLUOROSCOPIC IMAGE

FIG. 5B1

DRR IMAGE

FIRST DRR IMAGE

MEDICAL IMAGE PROCESSING DEVICE, STORAGE MEDIUM, MEDICAL DEVICE, AND TREATMENT SYSTEM

CROSS-REFERENCE TO RELATED APPLICATION

This application is based upon and claims the benefit of priority from Japanese Patent Application No. 2019-091410, filed May 14, 2019 and PCT/JP2020/018234, filed Apr. 30, 2020; the entire contents all of which are incorporated herein by reference.

FIELD

Embodiments of the present invention relate to a medical image processing device, a storage medium, a medical device, and a treatment system.

BACKGROUND

Radiation treatment is a treatment method of irradiating a lesion within a patient's body with radiation to destroy the lesion. At this time, the radiation is required to be accurately radiated to a position of the lesion. This is because, when normal tissue within the patient's body is irradiated with the radiation, the normal tissue may be affected. Thus, when the radiation treatment is performed, computed tomography (CT) is first performed in advance in a treatment planning stage and a position of the lesion within the patient's body is three-dimensionally ascertained. The radiation irradiation direction and the radiation irradiation intensity are planned to reduce irradiation of the normal tissue on the basis of the ascertained position of the lesion. Thereafter, the position of the patient in a treatment stage is aligned with the position of the patient planned in the treatment planning stage and a lesion is irradiated with radiation in accordance with an irradiation direction or an irradiation intensity planned in the treatment planning stage.

In the position alignment of the patient in the treatment stage, from three-dimensional CT data for the virtual arrangement in a treatment room, the position of the bed is adjusted so that the position of the patient actually laid on a movable bed in the treatment room matches the position of the three-dimensional CT data. More specifically, any misalignment of the patient between the images is obtained by collating two images including an X-ray fluoroscopic image of the inside of the patient's body photographed in a state in which the patient is laid on the bed and a digitally reconstructed radiograph (DRR) image in which the X-ray fluoroscopic image is virtually reconstructed from a three-dimensional CT image captured at the time of the treatment planning. At this time, X-ray fluoroscopic images of the patient are captured from at least two different directions so that the position of the patient is obtained in the three-dimensional space and the misalignment of the patient within the three-dimensional space is obtained by collating the X-ray fluoroscopic images with the DRR image. Finally, the bed is moved on the basis of the misalignment of the patient obtained in image collation and positions of lesions and bones in the patient's body are aligned at the time of the treatment planning.

Incidentally, in the radiation treatment, a lesion within the patient's body is irradiated with radiation a plurality of times. Thus, it is necessary to perform the alignment of the patient, i.e., the collation of the X-ray fluoroscopic image with the DRR image every time the lesion is irradiated with radiation. Here, the reconstruction of the DRR image from the three-dimensional CT image is performed by applying a ray tracing method to the data of the CT image, so that the calculation cost is high. That is, the creation of a DRR image is time-consuming. Also, a burden on the patient during the radiation treatment is heavy because the patient is restrained on the bed so that the position does not deviate every time the lesion is irradiated with radiation. Thus, in the related art, a method of shortening a time period required to align the position of the patient in the radiation treatment by automatically calculating the image collation between the X-ray fluoroscopic image and the DRR image in a calculator has been proposed.

In the conventional patient position alignment method, when the position alignment is performed with respect to each of the X-ray fluoroscopic images captured from two directions, a search process of collating the X-ray fluoroscopic image with the DRR image in one photography direction and a search process of collating the X-ray fluoroscopic image with the DRR image in the other photography direction are performed alternately. Thereby, in the conventional patient position alignment method, because of a change in the DRR image in the photography direction in which the search is in operation is small, it is not necessary to recreate the DRR image corresponding to the same photography direction and it is possible to speed up the search for a suitable position in each photography direction.

In the conventional patient alignment method, the calculation cost when the DRR image is created by reproducing a photography range, which is the same as that of the X-ray fluoroscopic image, in the DRR image is reduced. However, in recent years, the photography range of an X-ray fluoroscopic image has been reduced due to reasons such as cost reduction of an X-ray imaging device and restrictions on an installation location. A case in which a portion of a patient shown in an X-ray fluoroscopic image is not sufficiently included in a DRR image when there is a large difference between the position of the patient in the DRR image reconstructed from a CT image and the current position of the patient laid on the bed is taken into account. In this case, it may be difficult to obtain the misalignment of the patient in a process of collating the X-ray fluoroscopic image with the DRR image.

BRIEF DESCRIPTION OF THE DRAWINGS

FIG. 5B1 is a diagram showing a relationship between an X-ray fluoroscopic image and a reconstructed image generated by the medical image processing device in the treatment system of the first embodiment.

FIG. 5B2 is a diagram showing a relationship between an X-ray fluoroscopic image and a reconstructed image generated by the medical image processing device in the treatment system of the first embodiment.

FIG. 5B3 is a diagram showing a relationship between an X-ray fluoroscopic image and a reconstructed image generated by the medical image processing device in the treatment system of the first embodiment.

DETAILED DESCRIPTION

According to an aspect of the present embodiment, a medical image processing device includes a first image acquirer, a second image acquirer, a generator, and a calculator. The first image acquirer acquires a first fluoroscopic image of a patient. The second image acquirer acquires a second fluoroscopic image according to radiation with which the patient is irradiated at a time point different from a time point of acquisition of the first fluoroscopic image from a photography device that detects radiated radiation with a detector and performs an imaging process. The generator generates a reconstructed image obtained by reproducing the second fluoroscopic image from the first fluoroscopic image virtually arranged in a three-dimensional space on the basis of an installation position of the detector in the three-dimensional space. The calculator obtains a suitable position on the first fluoroscopic image in the three-dimensional space on the basis of a degree of similarity between the second fluoroscopic image and the reconstructed image. The generator generates the reconstructed image which is for use in the calculator and has a range larger than a range corresponding to the second fluoroscopic image.

Hereinafter, a medical image processing device, a storage medium, a medical device, and a treatment system of embodiments will be described with reference to the drawings.

First Embodiment

Figure 1:
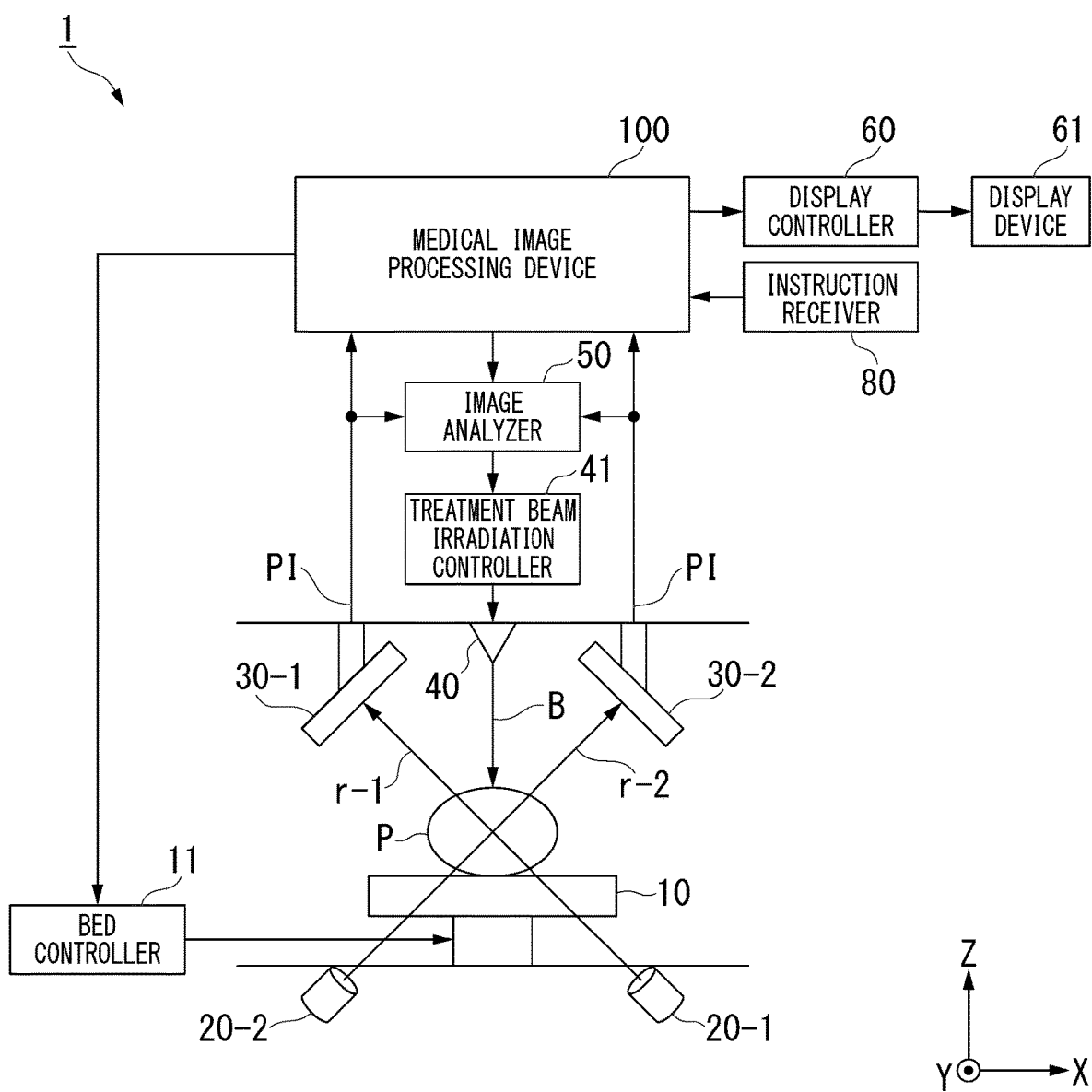
FIG. 1 is a block diagram showing a schematic configuration of a treatment system having a medical device including a medical image processing device of a first embodiment.

FIG. 1 is a block diagram showing a schematic configuration of a treatment system including a medical device including a medical image processing device of a first embodiment. The treatment system 1 includes, for example, a treatment table 10, a bed controller 11, two radiation sources 20 (a radiation source 20-1 and a radiation source 20-2), two radiation detectors 30 (a radiation detector 30-1 and a radiation detector 30-2), a treatment beam irradiation gate 40, a treatment beam irradiation controller 41, an image analyzer 50, a display controller 60, a display device 61, an instruction receiver 80, and a medical image processing device 100.

Also, a hyphen "-" indicated after a reference numeral shown in FIG. 1 and a number subsequent to the hyphen are used for identifying a corresponding relationship. More specifically, in the corresponding relationship between the radiation source 20 and the radiation detector 30, a state in which the radiation source 20-1 and the radiation detector 30-1 correspond to each other to form one set is shown and a state in which the radiation source 20-2 and the radiation detector 30-2 correspond to each other to form another set is shown. In the following description, when a plurality of identical components are represented without being distinguished, they are represented without the hyphen "-" and the number subsequent to the hyphen.

The treatment table 10 is a bed on which a subject (a patient) P that will undergo radiation treatment is fixed. The bed controller 11 is a controller that controls a translation mechanism and a rotation mechanism provided on the treatment table 10 so that a direction in which the patient P fixed on the treatment table 10 is irradiated with the treatment beam is changed. The bed controller 11 controls, for example, each of the translation mechanism and the rotation mechanism of the treatment table 10 in three-axial directions, i.e., six-axial directions.

The radiation source 20-1 radiates radiation r-1 for seeing through the body of the patient P at a predetermined angle. The radiation source 20-2 radiates radiation r-2 for seeing through the body of the patient P at a predetermined angle different from that of the radiation source 20-1. The radiation r-1 and the radiation r-2 are, for example, X-rays. In FIG. 1, a case in which X-ray photography is performed from two directions on the patient P fixed on the treatment table 10 is shown. Also, the illustration of a controller that controls the irradiation with the radiation r by the radiation source 20 is omitted from FIG. 1.

The radiation detector 30-1 detects the radiation r-1 which has been radiated from the radiation source 20-1 and has arrived at the radiation detector 30-1 after passing through the inside of the body of the patient P and generates an X-ray fluoroscopic image PI of the inside of the body of the patient P according to a magnitude of energy of the detected radiation r-1. The radiation detector 30-2 detects the radiation r-2 which has been radiated from the radiation source 20-2 and has arrived at the radiation detector 30-2 after passing through the inside of the body of the patient P and generates an X-ray fluoroscopic image PI of the inside of the body of the patient P according to a magnitude of energy of the detected radiation r-2. The radiation detectors 30 are X-ray detectors arranged in a two-dimensional array shape and generate a digital image in which a magnitude of energy of the radiation r arriving at each X-ray detector is represented by a digital value as an X-ray fluoroscopic image PI. The radiation detector 30 is, for example, a flat panel detector (FPD), an image intensifier, or a color image intensifier. In the following description, each radiation detector 30 is assumed to be an FPD. The radiation detector 30 (the FPD) outputs the generated X-ray fluoroscopic image PI to the medical image processing device 100. Also, the illustration of a controller that controls the generation of the X-ray fluoroscopic image PI by the radiation detector 30 is omitted from FIG. 1.

In the treatment system 1, a set of the radiation source 20 and the radiation detector 30 is an example of a "photography device" in the claims. In FIG. 1, a photography device, which captures X-ray fluoroscopic images PI of the patient P from two different directions, is shown. A combination of the photography device and the medical image processing device 100 is an example of a "medical device" in the claims.

In the treatment system 1, because the positions of the radiation source 20 and the radiation detector 30 are fixed, a direction of a photography process of the photography device including the set of the radiation source 20 and the radiation detector 30 (a relative direction associated with a fixed coordinate system of the treatment room) is fixed. Thus, when the three-dimensional coordinates are defined within a three-dimensional space where the treatment system 1 is installed, positions of the radiation source 20 and the radiation detector 30 can be represented by coordinate values of three axes. In the following description, information about the coordinate values of the three axes is referred to as geometry information of the photography device including the set of the radiation source 20 and the radiation detector 30. If the geometry information is used, the position of the patient P located at any position within prescribed three-dimensional coordinates can be obtained from a position where the radiation radiated from the radiation source 20 has passed through the body of the patient P and has arrived at the radiation detector 30. That is, the position of the patient P in the prescribed three-dimensional coordinates can be obtained as a projection matrix.

The geometry information can be obtained from the installation positions of the radiation source 20 and the radiation detector 30 designed when the treatment system 1 is installed. The geometry information can also be obtained from the installation positions of the radiation source 20 and the radiation detector 30 measured by a three-dimensional measurement instrument or the like. By obtaining the projection matrix from the geometry information, the medical image processing device 100 can calculate a position where the patient P in the three-dimensional space is photographed in the captured X-ray fluoroscopic image PI.

Also, in the photography device that simultaneously captures two X-ray fluoroscopic images PI of the patient P as shown in FIG. 1, a projection matrix is obtained for each set of the radiation source 20 and the radiation detector 30. Thereby, it is possible to calculate a coordinate value in prescribed three-dimensional coordinates representing a position of a lesion or a bone or a marker from a position (a position of two-dimensional coordinates) of an image of the lesion or the bone in the body of the patient P photographed in two X-ray fluoroscopic images PI or the marker placed in the body of the patient P in advance as in the principle of triangulation.

Also, in FIG. 1, the configuration of the treatment system 1 including the two sets of the radiation sources 20 and the radiation detectors 30, i.e., two photography devices, is shown. However, the number of photography devices included in the treatment system 1 is not limited to two. For example, the treatment system 1 may include three or more photography devices (three or more sets of radiation sources 20 and radiation detectors 30). Also, the treatment system 1 may include only one photography device (a set of a radiation source 20 and a radiation detector 30).

The treatment beam irradiation gate 40 is an irradiator that irradiates the patient P with radiation for destroying a lesion, which is a treatment target portion in the body of the patient P, as the treatment beam B. The treatment beam B is, for example, an X-ray, a γ-ray, an electron beam, a proton beam, a neutron beam, a heavy particle beam, or the like. The treatment beam B is linearly radiated from the treatment beam irradiation gate 40 to the patient P (more specifically, the lesion in the body of the patient P). The treatment beam irradiation controller 41 controls the irradiation with the treatment beam B by the treatment beam irradiation gate 40. The treatment beam irradiation controller 41 causes the treatment beam irradiation gate 40 to radiate the treatment beam B in response to a signal output by the image analyzer 50 indicating an irradiation timing of the treatment beam B. Although a configuration of the treatment system 1 including one fixed treatment beam irradiation gate 40 is shown in FIG. 1, the present invention is not limited thereto and the treatment system 1 may include a plurality of treatment beam irradiation gates. For example, the treatment system 1 may further include a treatment beam irradiation gate that irradiates the patient P with the treatment beam from a horizontal direction. Also, the treatment system 1 may be configured to irradiate the patient P with treatment beams from various directions by rotating one treatment beam irradiation gate around the patient P. More specifically, the treatment beam irradiation gate 40 shown in FIG. 1 may be configured to be able to rotate 360 degrees with respect to a rotation axis in a horizontal direction Y shown in FIG. 1. The treatment system 1 having the above configuration is called a rotary gantry type treatment system. Also, in the rotary gantry type treatment system, the radiation source 20 and the radiation detector 30 also rotate 360 degrees at the same time with respect to an axis which is the same as the rotation axis of the treatment beam irradiation gate 40.

The image analyzer 50 tracks a position of an organ such as the lung or the liver that moves due to the motion of the patient P's respiration and heartbeat and determines an irradiation timing for irradiating the patient P's lesion with the treatment beam B. That is, the image analyzer 50 determines the irradiation timing of the treatment beam B for performing radiation treatment in a respiratory synchronous irradiation method. The image analyzer 50 automatically determines an irradiation timing of the treatment beam B with which a lesion is irradiated in the radiation treatment by tracking an image of a lesion or a bone in the body of patient P captured in the X-ray fluoroscopic image PI of the patient P photographed in real time by each radiation detector 30. At this time, the image analyzer 50 determines whether or not the position of the image of the lesion or the bone in the body of the patient P being tracked is within a prescribed range (region) (hereinafter referred to as "gate window") for performing radiation treatment, designates a timing when the position of the image of the lesion or the bone in the body of the patient P is within the gate window as an irradiation timing when the treatment beam B is radiated, and outputs a signal indicating the irradiation timing to the treatment beam irradiation controller 41. Thereby, the treatment beam irradiation controller 41 causes the treatment beam irradiation gate 40 to radiate the treatment beam B in response to the signal output by the image analyzer 50 indicating the irradiation timing. That is, the treatment beam irradiation controller 41 controls the treatment beam irradiation gate 40 so that the treatment beam irradiation gate 40 radiates the treatment beam B only when the position of the image of the lesion or bone in the body of the patient P being tracked is within the gate window and controls the treatment beam irradiation gate 40 so that the irradiation with the treatment beam B is stopped when the position of the image of the lesion or bone in the body of the patient P being tracked is not within the gate window.

Also, the gate window is centered on a position of a lesion or a bone in the body of patient P shown in the three-dimensional computed tomography (CT) image CI captured before the radiation treatment is performed and a three-dimensional region where a margin is added to the center position is set. Also, the gate window may be set by designating a range (a region) set for the CT image CI as a range (a region) projected onto a digitally reconstructed radiograph (DRR) image DI obtained by virtually reconstructing the X-ray fluoroscopic image PI from the CT image CI or the X-ray fluoroscopic image PT. Also, the gate window may be set by adding a margin set in consideration of a state of the patient P immediately before the radiation treatment is started. By setting the gate window in consideration of the above process, it is possible to avoid a situation in which the patient P is irradiated with an inappropriate treatment beam B or unnecessary radiation r, i.e., so-called radiation exposure.

Also, the image analyzer 50 may automatically determine the irradiation timing of the treatment beam B with which the lesion is irradiated in the radiation treatment from a relationship between relative positions of the marker and the lesion and the like by tracking the image of the marker placed in the body of the patient P in advance to be treated in the radiation treatment on the basis of the X-ray fluoroscopic image PI captured in real time by each radiation detector 30. In this case, the image analyzer 50 outputs a signal indicating a timing when the position of the image of the marker being tracked is within the gate window as the irradiation timing when the treatment beam B is radiated to the treatment beam irradiation controller 41.

The medical image processing device 100 is a processor that performs image processing for determining a position to align the current position of the patient P with a predetermined position in a planning stage before radiation treatment is performed such as a treatment planning stage. The medical image processing device 100 automatically searches for the position of the patient P suitable for performing radiation treatment by collating a DRR image DI obtained by virtually reconstructing an X-ray fluoroscopic image PI from a three-dimensional CT image CI or the like captured in advance before radiation treatment is performed with a current X-ray fluoroscopic image PI output by each radiation detector 30. The medical image processing device 100 obtains the amount of movement of the treatment table 10 by moving the current position of the patient P fixed on the treatment table 10 to a predetermined suitable position (hereinafter referred to as a "suitable position") for performing radiation treatment. Details regarding a configuration and a process of the medical image processing device 100 will be described below.

Also, each of the medical image processing device 100 and the radiation detector 30 may be a component connected by a local area network (LAN) or a wide area network (WAN).

The display controller 60 causes the display device 61 to display a CT image CI, a DRR image DI, and an X-ray fluoroscopic image PI and further display information about the current suitable position during a process of searching for the suitable position in the medical image processing device 100. Thereby, for example, the display device 61 such as a liquid crystal display (LCD) displays the CT image CI, the DRR image DI, the X-ray fluoroscopic image PI, and the information about the current suitable position and the radiation treatment practitioner (a doctor or the like) using the treatment system 1 can visually check a current position determination situation.

The instruction receiver 80 is a user interface for the radiation treatment practitioner (the doctor or the like) using the treatment system 1 to manually adjust a suitable position found in the search process of the medical image processing device 100. The instruction receiver 80 includes an operator (not shown) that is operated by the radiation treatment practitioner (the doctor or the like).

Also, the medical image processing device of the first embodiment may have a configuration including the medical image processing device 100, the display controller 60, and the instruction receiver 80. Also, the medical image processing device of the first embodiment may be configured to further include the image analyzer 50. Also, the medical image processing device of the first embodiment may be configured to be further integrated with the display device 61.

Figure 2:
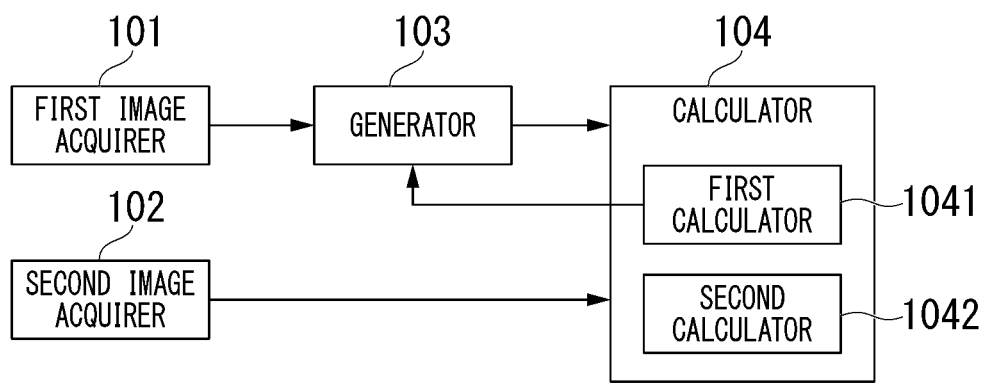
FIG. 2 is a block diagram showing a schematic configuration of the medical image processing device of the first embodiment.

Next, a configuration of the medical image processing device 100 constituting the treatment system 1 will be described. FIG. 2 is a block diagram showing a schematic configuration of the medical image processing device 100 of the first embodiment. The medical image processing device 100 shown in FIG. 2 includes a first image acquirer 101, a second image acquirer 102, a generator 103, and a calculator 104. Also, the calculator 104 includes a first calculator 1041 and a second calculator 1042.

The first image acquirer 101 acquires a three-dimensional volume data image for enabling the body of the patient P to be treated to be seen through. The first image acquirer 101 outputs the acquired three-dimensional volume data to the generator 103. The three-dimensional volume data is three-dimensional data acquired by photographing the patient P with a photography device such as a CT device, a cone-beam (CB) CT device, or a magnetic resonance imaging (MRI) device. In the following description, it is assumed that the three-dimensional volume data is the data of the CT image CI (hereinafter referred to as "CT data") acquired by photographing the patient P with the CT device.

The second image acquirer 102 acquires an X-ray fluoroscopic image PI of the inside of the body of the current patient P fixed on the treatment table 10 in the treatment room where the treatment system 1 is installed. That is, the second image acquirer 102 acquires the X-ray fluoroscopic image PI of the inside of the body of the patient P photographed in real time by each radiation detector 30. The second image acquirer 102 outputs the acquired X-ray fluoroscopic image PI to the calculator 104.

The generator 103 generates a DRR image DI on the basis of the CT data output by the first image acquirer 101. At this time, the generator 103 generates a DRR image DI (hereinafter referred to as a "first DRR image DI1") obtained by virtually enlarging a size of the FPD, i.e., a photography range of the FPD, along a two-dimensional plane parallel to a plane on which each of the two radiation detectors 30 (FPDs) constituting the photography device in the treatment system 1 detects radiation and a DRR image DI (hereinafter referred to as a "second DRR image DI2") having a photography range that is the same as the photography ranges of the two FPDs. The generator 103 outputs each of the first DRR image DI1 and the second DRR image DI2, which have been generated, to the calculator 104.

The calculator 104 calculates misalignment (hereinafter referred to as "the amount of misalignment of the patient P) between a position (hereinafter referred to as a "CT position") of CT data virtually arranged within the three-dimensional space of the treatment room where the treatment system 1 is installed and the current position of the patient P fixed on the treatment table 10 on the basis of the first DRR image DI1 or the second DRR image DI2 generated by the generator 103 and the X-ray fluoroscopic image PT acquired by the second image acquirer 102. The calculator 104 searches for a CT position having the smallest amount of misalignment of the patient P as a suitable position on the basis of the calculated amount of misalignment of the patient P. The calculator 104 calculates six control parameters for causing the treatment table 10 to perform rotation and translation based on the three-dimensional coordinates within the treatment room on the basis of the CT position of the suitable position found in the search and outputs the six control parameters, which have been calculated, to the bed controller 11. Here, the six control parameters output by the calculator 104 to the bed controller 11 are parameters for controlling each of the translation mechanism and the rotation mechanism provided on the treatment table 10 in three-axial directions.

The first calculator 1041 searches for a CT position having the smallest amount of misalignment of the patient P while a CT position where the amount of misalignment of the patient P is calculated is moved along a two-dimensional plane parallel to a plane on which the radiation detector 30 (the FPD) detects radiation on the basis of the first DRR image DI1 and the X-ray fluoroscopic image PI. For example, the first calculator 1041 causes the CT position to be moved in accordance with one parameter representing the amount of translation based on three-dimensional coordinates within the treatment room and searches for a CT position having the highest degree of similarity between the first DRR image DI1 and the X-ray fluoroscopic image P1. The first calculator 1041 searches for the CT position until the amount of misalignment of the patient P is within a prescribed range. At this time, the first calculator 1041 alternately performs the search for the CT position based on the first DRR image DI1 corresponding to one of the radiation detector 30-1 and the radiation detector 30-2 and the X-ray fluoroscopic image PI and the search for the CT position based on the first DRR image DI1 corresponding to the other of the radiation detector 30-1 and the radiation detector 30-2 and the X-ray fluoroscopic image PI. Therefore, the search for the CT position in the first calculator 1041 may be completed after only the search for the CT position corresponding to one radiation detector 30, i.e., one process, but may be completed after the search for the CT position corresponding to one radiation detector 30 and the search for the CT position corresponding to the other radiation detector 30 are alternately iterated a plurality of times. The search for the CT position in the first calculator 1041 is a simple CT position search that is performed until the amount of misalignment of the patient P is within a prescribed range, i.e., until the position of the patient P fixed on the treatment table 10 can be adjusted to some extent. In the following description, a search for the CT position in the first calculator 1041 is referred to as a "sparse search."

In the sparse search for the CT position in the first calculator 1041, as described above, the search for the CT position based on the first DRR image DI1 corresponding to one radiation detector 30 and the X-ray fluoroscopic image PI and the search for the CT position based on the first DRR image DI1 corresponding to the other radiation detector 30 and the X-ray fluoroscopic image PI are alternately performed. Thus, the first calculator 1041 outputs information about the CT position having the smallest amount of misalignment of the patient P subjected to the sparse search to the generator 103 every time the sparse search of the CT position using the current first DRR image DI1 is completed. Thereby, the generator 103 generates a new First DRR image DI1 corresponding to the radiation detector 30 different from the radiation detector 30 corresponding to the current first DRR image DI1 on the basis of the CT position in the current first DRR image DI1 output by the first calculator 1041 and outputs the new first DRR image DI1, which has been generated, to the first calculator 1041. In this way, the generator 103 and the first calculator 1041 cooperate with each other to generate the first DRR image DI1 and perform a sparse search for the CT position until the amount of misalignment of the patient P is within a prescribed range.

Following the first calculator 1041, the second calculator 1042 searches for the CT position having the smallest amount of misalignment of the patient P in more detail. The second calculator 1042 searches for a CT position having the smallest amount of misalignment of the patient P while the CT position where the amount of misalignment of the patient P is calculated is moved in a rotation direction and a translation direction based on three-dimensional coordinates within the treatment room on the basis of the second DRR image DI2 based on the CT position where the amount of misalignment of the patient P found in the search in the first calculator 1041 is smallest and the X-ray fluoroscopic image PI. In other words, the second calculator 1042 causes the CT position to be moved in accordance with six parameters representing the amount of rotation and the amount of translation based on the three-dimensional coordinates within the treatment room and searches for a CT position having the highest degree of similarity between the second DRR image DI2 and the X-ray fluoroscopic image PT as a final suitable position. Also, the search for the CT position in the second calculator 1042 is a detailed CT position search for automatically determining the final CT position (suitable position), i.e., a direction in which the patient P fixed on the treatment table 10 is irradiated with the treatment beam B, on the basis of the second DRR image DI2 and the X-ray fluoroscopic image PI. In the following description, the search for the CT position in the second calculator 1042 is referred to as a "dense search." The second calculator 1042 calculates six control parameters for causing the treatment table 10 to perform rotation and translation according to the three-dimensional coordinates within the treatment room on the basis of the final suitable position (CT position) found in the search. The calculated six control parameters are output to the bed controller 11.

Thereby, the bed controller 11 controls the translation mechanism and the rotation mechanism provided on the treatment table 10 in accordance with the six control parameters output by the second calculator 1042 and sets a direction suitable for performing the radiation treatment by radiating the treatment beam B as the direction of the patient P fixed on the treatment table 10.

According to the above configuration, the medical image processing device 100 calculates the six control parameters for setting a suitable direction as the direction of the patient P fixed on the treatment table 10 according to the sparse search in the first calculator 1041 and the dense search in the second calculator 1042. Thereby, in the treatment system 1 including the medical image processing device 100, it is possible to set a direction suitable for radiating the treatment beam B as the direction of the patient P to be treated in the radiation treatment in accordance with the six control parameters calculated by the medical image processing device 100. In the treatment system 1 including the medical image processing device 100, the treatment beam B can be radiated to a lesion in the body of the patient P at an appropriate timing determined by the image analyzer 50.

Also, for some or all of the functions of the components provided in the medical image processing device 100 described above, for example, a hardware processor such as a central processing unit (CPU) and a storage device (a storage device including a non-transitory storage medium) storing a program (software), are provided and various types of functions may be implemented by the processor executing the program. Also, functions of some or all of the components provided in the above-described medical image processing device 100 may be implemented by hardware (including a circuit unit; circuitry) such as a large-scale integration (LSI) circuit, an application specific integrated circuit (ASIC), a field-programmable gate array (FPGA), or a graphics processing unit (GPU) or various types of functions may be implemented by software and hardware in cooperation. Also, for some or all of the functions of the components provided in the medical image processing device 100 described above, various types of functions may be implemented by a dedicated LSI. Here, the program (software) may be pre-stored in a storage device (a storage device including a non-transitory storage medium) provided in the treatment system 1 such as a read only memory (ROM), a random-access memory (RAM), a hard disk drive (HDD), or a flash memory or may be stored in a removable storage medium (a non-transitory storage medium) such as a DVD or a CD-ROM and installed in the storage device provided in the treatment system 1 when the storage medium is mounted in a drive device provided in the treatment system 1. Also, the program (software) may be downloaded in advance from another computer device via the network and installed in the storage device provided in the treatment system 1.

Figure 3:
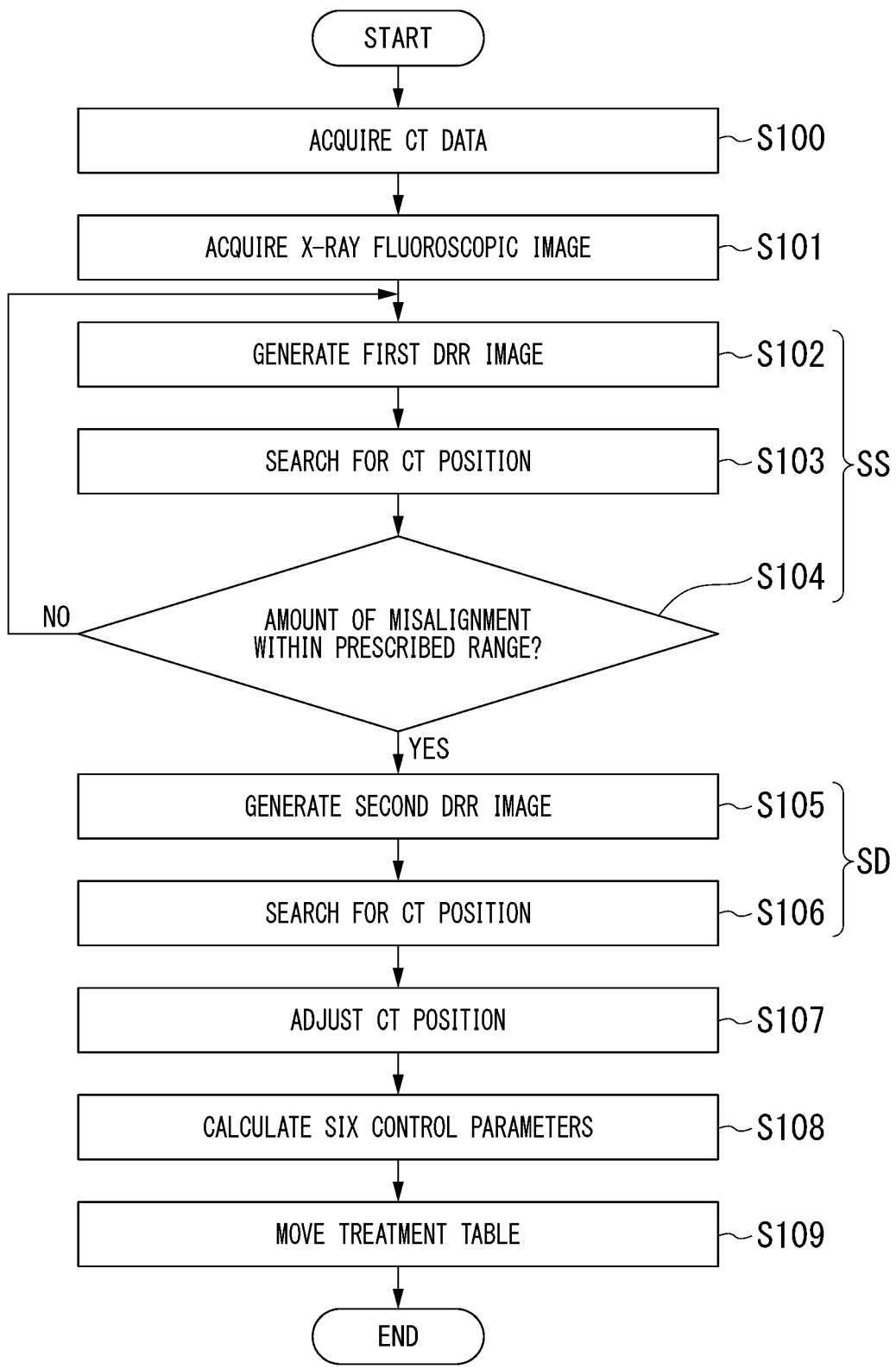
FIG. 3 is a flowchart showing a flow of an operation in the treatment system of the first embodiment.

Next, the outline of the operation of the treatment system 1 will be described. FIG. 3 is a flowchart showing a flow of an operation of the treatment system 1 of the first embodiment. Also, in the following description, it is assumed that the patient P is photographed in advance by a CT device and CT data (three-dimensional volume data) of a CT image CI is provided. Also, it is assumed that the first calculator 1041 and the second calculator 1042 search for a CT position on the basis of a degree of similarity between a DRR image DI and an X-ray fluoroscopic image PI.

When the treatment system 1 starts an operation and the medical image processing device 100 is activated, the first image acquirer 101 acquires CT data (step S100). The first image acquirer 101 outputs the acquired CT data to the generator 103.

Subsequently, the second image acquirer 102 acquires an X-ray fluoroscopic image PI of the inside of the body of the current patient P output by each radiation detector 30 (step S101). The second image acquirer 102 outputs the acquired X-ray fluoroscopic image PI to the calculator 104.

Subsequently, the medical image processing device 100 starts a process of a sparse search SS for the CT position. In the process of the sparse search SS for the CT position, the generator 103 generates a first DRR image DI1 on the basis of the CT data output by the first image acquirer 101 (step S102). The generator 103 outputs the generated first DRR image DI1 to the calculator 104.

Subsequently, the first calculator 1041 within the calculator 104 searches for a CT position having the highest degree of similarity between the current first DRR image DI1 and the X-ray fluoroscopic image PI on the basis of the first DRR image DI1 output by the generator 103 and the X-ray fluoroscopic image PI output by the second image acquirer 102 (step S103).

Subsequently, the first calculator 1041 determines whether or not the amount of misalignment of the patient P at the CT position found in the search is within a prescribed range (step S104). In step S104, when the amount of misalignment of the patient P at the CT position found in the search is not within the prescribed range, the first calculator 1041 outputs information about the CT position found in the search to the generator 103, and the process returns to step S102. Thereby, the generator 103 generates a new first DRR image DI1 on the basis of information about the CT position output by the first calculator 1041 in step S102 and the first calculator 1041 searches for the CT position having the highest degree of similarity between the new first DRR image DI1 and the X-ray fluoroscopic image PI on the basis of the new first DRR image DI1 generated by the generator 103 and the X-ray fluoroscopic image PI output by the second image acquirer 102 in step S103. In this way, in the medical image processing device 100, the generator 103 and the first calculator 1041 cooperate with each other and iterates the process of the sparse search SS for the CT position until the amount of misalignment of the patient P at the CT position found in the search is within the prescribed range, i.e., until the degree of similarity between the first DRR image DI1 and the X-ray fluoroscopic image PI becomes higher than a prescribed threshold value for the degree of similarity.

On the other hand, when the amount of misalignment of the patient P at the CT position found in the search is within the prescribed range, i.e., when a CT position where the degree of similarity between the first DRR image DI1 and the X-ray fluoroscopic image PI becomes higher than the prescribed threshold value for the degree of similarity has been found in the search, in step S104, the first calculator 1041 outputs the CT position found in the search information to the second calculator 1042 and moves the process to step S105.

Thereby, the medical image processing device 100 starts the process of a dense search SD for the CT position. In the process of the dense search SD for the CT position, the generator 103 generates a second DRR image DI2 on the basis of the CT data output by the first image acquirer 101 (step S105). The generator 103 outputs the second DRR image DI2, which has been generated, to the calculator 104.

Subsequently, the second calculator 1042 searches for a final CT position on the basis of the second DRR image DI2 output by the generator 103 and the X-ray fluoroscopic image PI output by the second image acquirer 102 with respect to the CT position found in the search in the first calculator 1041 (step S106). As described above, in the medical image processing device 100, the second calculator 1042 performs the process of the dense search SD for the CT position only once.

Subsequently, the display controller 60 causes the display device 61 to display the second DRR image DI2 output by the generator 103 and the X-ray fluoroscopic image PI output by the second image acquirer 102. Further, the display controller 60 causes the display device 61 to display the final CT position found in the search in the second calculator 1042. The instruction receiver 80 receives the final CT position adjusted by the radiation treatment practitioner (the doctor or the like) using the treatment system 1 and outputs adjustment information about the final CT position, which has been received, to the second calculator 1042 (step S107).

Subsequently, the second calculator 1042 reflects the adjustment information of the final CT position output by the instruction receiver 80 in the CT position found in the search and sets an adjusted position as the final CT position (a suitable position). The second calculator 1042 calculates six control parameters for causing the treatment table 10 to perform rotation and translation according to three-dimensional coordinates within the treatment room (step S108). The second calculator 1042 outputs the calculated six control parameters to the bed controller 11.

Subsequently, the bed controller 11 moves the treatment table 10 in accordance with the six control parameters output by the second calculator 1042 (step S109).

Next, details of the operation of the medical image processing device 100 constituting the treatment system 1 will be described. First, a method of generating a DRR image DI in the generator 103 constituting the medical image processing device 100 will be described. The DRR image DI is an image generated for virtually simulating the X-ray fluoroscopic image PI. Thus, a photography model of the X-ray fluoroscopic image PI will be first described and a method of generating a DRR image DI will be subsequently described.

(Photography Model for X-Ray Fluoroscopic Image)

In X-ray photography, it is possible to obtain an X-ray fluoroscopic image PT for seeing through the body of the patient P by imaging a magnitude of energy when X-rays radiated by the radiation source 20 which is an X-ray source pass through the body of the patient P who is a subject and arrive at the radiation detector 30 which is the FPD in which the X-ray detectors are arranged in a two-dimensional array. X-ray energy $P_i$ at each pixel position in the X-ray fluoroscopic image PI, i.e., the position of the X-ray detector, can be expressed by the following Eq. (1).

[Math. 1]

$$P_i = P_0 \exp\{-\oint \mu(l,P)dl\} \quad (1)$$

In the above Eq. (1), $P_0$ is the energy of X-rays when the X-rays are incident on the subject (the patient P). Also, in the above Eq. (1), $\mu(l, P)$ is a linear attenuation coefficient of a physical object at a position l and is a value that changes with energy P of the X-rays passing through a substance thereof. A result of performing a line integral on linear attenuation coefficients of the substance on an X-ray path until X-rays arrive at a pixel position i from the X-ray source is the energy of the X-rays reaching the X-ray detector. Here, detection characteristics of the X-ray detector are designed to be linear with respect to a logarithmic value of the X-ray energy $P_i$ and an image can be obtained by linearly converting a signal value output by the X-ray detector into a pixel value. That is, a pixel value $T_i$ of the X-ray fluoroscopic image PI can be expressed by the following Eq. (2).

[Math. 2]

$$T_i(P_0) = \log(P_i) = \log(P_0) - \oint \mu(l,P)dl \quad (2)$$

In the above Eq. (2), $\log(P_0)$ is a constant. Thus, each pixel in the X-ray fluoroscopic image PI obtained in X-ray photography is imaged in accordance with a product-sum operation on linear attenuation coefficients of the substance (i.e., the patient P) on the path along which X-rays radiated from the X-ray source arrive at each X-ray detector constituting the FPD.

(DRR Image Generation Method)

Figure 4:
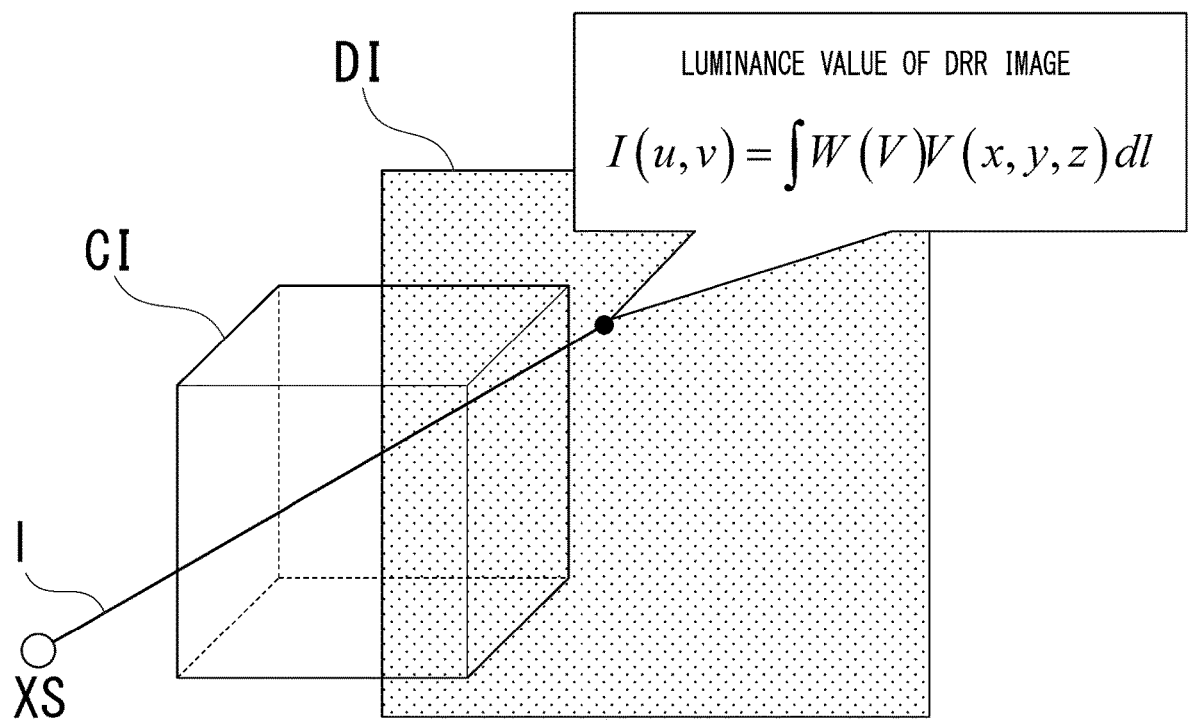
FIG. 4 is a diagram showing relationships between an irradiation path of radiation and a computed tomography image and a digitally reconstructed radiograph image generated by the medical image processing device in the treatment system of the first embodiment.

Next, a method of generating the DRR image DI will be described. The DRR image DI is generated by performing perspective projection on a CT image CT virtually arranged in a three-dimensional space from any direction. Here, an example of a process of generating the DRR image DI is shown in FIG. 4. FIG. 4 is a diagram showing relationships between an irradiation path of radiation (X-rays) in the treatment system 1 of the first embodiment and a computed tomography image (a CT image CI) and a digitally reconstructed radiograph image (a DRR image DI) generated by the medical image processing device 100. In FIG. 4, a pixel position on the coordinate system of the photography device in the treatment system 1 is (x, y, z) and the pixel position on the coordinate system of the DRR image DI is (u, v). A luminance value I(u, v) of the DRR image DI at the pixel position (u, v) is calculated by a ray tracing equation represented by the following Eq. (3).

[Math. 3]

$$I(u,v) = \oint W(V)V(x,y,z)dl \quad (3)$$

In the above Eq. (3), V(x, y, z) is a CT value at the pixel position (x, y, z) of the CT image CI virtually arranged in the treatment system 1. In the above Eq. (3), the luminance value I(u, v) of the DRR image DI is obtained by integrating CT values on the irradiation path l of the X-rays radiated from an X-ray source XS. Here, W(V) in the above Eq. (3) is a weighting coefficient multiplied by the CT value. By controlling the weighting coefficient W(V), it is possible to generate a DRR image DI in which a specific CT value is highlighted. This is effective at the time when visibility is improved by highlighting the tissue of the lesion of the patient P desired to be emphasized or highlighting the tissue to which the radiation treatment practitioner (the doctor or the like) wants to pay attention if the X-ray fluoroscopic image PI is collated with the DRR image DI.

Here, the CT value V(x, y, z) included in the luminance value I(u, v) of the DRR image DI is a value based on the linear attenuation coefficient of the substance at the pixel position (x, y, z). Thus, when the DRR image DI is generated by a sum of the linear attenuation coefficients of the substances in the X-ray irradiation path l, a pixel value of the X-ray fluoroscopic image PI is also determined by the sum of the linear attenuation coefficients on the X-ray irradiation path l as shown in the above Eq. (3) and the X-ray fluoroscopic image PT is similar to the DRR image DI. Also, it is necessary to determine the positions of the X-ray irradiation path l and the CT value V(x, y, z) so that the X-ray fluoroscopic image PI is reconstructed from the CT value like the DRR image DI.

Next, the search for the CT position (the suitable position) in the calculator 104 constituting the medical image processing device 100, i.e., the first calculator 1041 and the second calculator 1042, will be described. First, the concept of the search for the CT position (suitable position) common to the first calculator 1041 and the second calculator 1042 will be described under the assumption that the calculator 104 searches for a CT position (suitable position).

The calculator 104 defines an evaluation function for calculating the degree of similarity based on values of pixels (pixel values) constituting each of the DRR image DI and the X-ray fluoroscopic image PI and searches for a CT position (a suitable position) by obtaining a pixel position where an image having the best evaluation value (the highest degree of similarity) is captured. More specifically, a position associated with the best evaluation function output (the degree of similarity) obtained from the pixel values of each of the DRR image DI and the X-ray fluoroscopic image PI is searched for while the CT position determined by the six parameters for determining a position and an orientation of the CT data within the three-dimensional space is moved. At this time, the calculator 104 uses a normalized cross-correlation of the pixel values of the two images of the DRR image DI and the X-ray fluoroscopic image PI as the evaluation function. Also, the calculator 104 may use a mutual information amount of pixel values of the two images of the DRR image DI and the X-ray fluoroscopic image PI as an evaluation function. Also, the calculator 104 may temporarily convert the two images of the DRR image DI and the X-ray fluoroscopic image PI into images processed using a Gaussian filter, a Sobel filter, or the like and use a difference between the converted images, a normalized cross-correlation, or a mutual information amount as the evaluation function. Also, the calculator 104 may perform conversion into an image obtained by calculating a gradient direction of each pixel constituting the two images of the DRR image DI and the X-ray fluoroscopic image PI and set a degree of coincidence of the gradient direction of each pixel after the conversion as the evaluation function.

On the basis of the above concept, the calculator 104 (the first calculator 1041 and the second calculator 1042) searches for a CT position (a suitable position) using the DRR image DI and the X-ray fluoroscopic image PI. Also, in the conventional general treatment system, when the evaluation function for calculating the degree of similarity as described above is used in the search for the CT position (the suitable position), it is assumed that the same portion in the body of the patient P is shown within the photography ranges of the two images. However, the calculator 104 searches for the CT position (the suitable position) in the sparse search in the first calculator 1041 and the dense search in the second calculator 1042, i.e., a two-step search. Thereby, the calculator 104 can search for the CT position (the suitable position) with high accuracy even if the photography range of the radiation detector 30 (the FPD) is decreased due to the cost reduction of the photography device constituting the treatment system 1, the limitation of an installation location, or the like and there is a large difference between a portion inside the body of the patient P shown in a DRR image DI and a portion inside the body of the patient P shown in an X-ray fluoroscopic image P1. That is, the calculator 104 can perform a process of determining the position of the patient P with high accuracy.

Next, the sparse search for the CT position (the suitable position) in the first calculator 1041 will be described. As described above, the first calculator 1041 searches for a CT position where the amount of misalignment of the patient P is smallest on the basis of the first DRR image DI1 obtained by the generator 103 virtually enlarging a size of the FPD along a two-dimensional plane parallel to a plane on which the radiation detector 30 (the FPD) detects radiation and the X-ray fluoroscopic image PI. Thus, an example of the first DRR image DI1 generated by the generator 103 will be first described and a sparse search method for the CT position (the suitable position) in the first calculator 1041 will be subsequently described.

(First DRR Image)

Figure 5A:
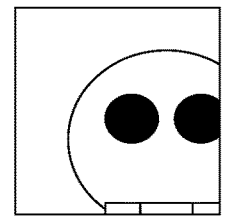
FIG. 5A is a diagram showing a relationship between an X-ray fluoroscopic image and a reconstructed image generated by the medical image processing device in the treatment system of the first embodiment.
Figure 5A:
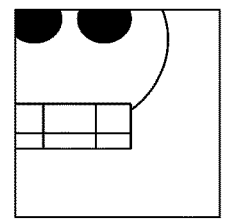
Figure 5A:
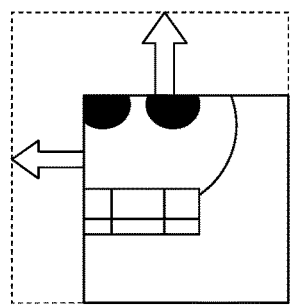
Figure 5A:
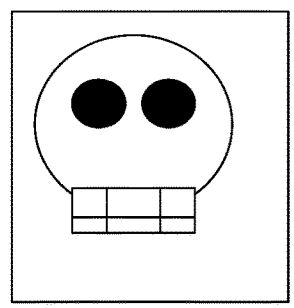

FIGS. 5A, 5B1, 5B2, and 5B3 are diagrams showing a relationship between the X-ray fluoroscopic image PI in the treatment system 1 of the first embodiment and the reconstructed image (a first DRR image DI1) generated by the generator 103 provided in the medical image processing device 100. An example of the X-ray fluoroscopic image PI output by one of the radiation detectors 30 acquired by the second image acquirer 102 is shown in FIG. 5A and an example of a process when the generator 103 generates the first DRR image DI1 corresponding to the X-ray fluoroscopic image PI shown in FIG. 5A is shown in FIGS. 5B1, 5B2, and 5B3. An example of the DRR image DI generated by the generator 103 is shown in FIG. 5B1, a diagram showing an example of a process performed when the generator 103 generates the first DRR image DI1 is shown in FIG. 5B2, and an example of the first DRR image DI1 generated by the generator 103 is shown in FIG. 5B3. In the following description, it is assumed that the X-ray fluoroscopic image PI shown in FIG. 5A and the first DRR image DI1 shown in FIG. 5B3 are images corresponding to the radiation detector 30-1.

As in the conventional general treatment system, the second image acquirer 102 acquires an X-ray fluoroscopic image PI obtained by the radiation detector 30-1 photographing the inside of the body of the current patient P fixed on the treatment table 10 in the treatment room where the treatment system 1 is installed. Here, for example, the DRR image DI as shown in FIG. 5B1 may be generated if the generator 103 generates a DRR image DI of a range which is the same as the photography range of the radiation detector 30-1 as in the conventional general treatment system. In this case, as can be seen by comparing FIG. 5A and FIG. 5B1, a case in which a portion of the patient P shown in the X-ray fluoroscopic image PT shown in FIG. 5A and a portion of the patient P shown in the DRR image DI shown in FIG. 5B1 significantly deviate is also taken into account. In the DRR image DI shown in FIG. 5B1, a center position is significantly shifted to the upper left with respect to the X-ray fluoroscopic image PI shown in FIG. 5A which is captured so that the position of the lesion to be irradiated with the treatment beam B is substantially centered and the upper portion of the head of the patient P is not shown. Then, a region of a portion of the patient P commonly included in the X-ray fluoroscopic image PI shown in FIG. 5A and the DRR image DI shown in FIG. 5B1 is reduced and it may be difficult to calculate the amount of displacement of the patient P. That is, it is not possible to calculate an evaluation value (a degree of similarity) based on the evaluation function obtained from the pixel values of the X-ray fluoroscopic image PI shown in FIG. 5A and the DRR image DI shown in FIG. 5B1 and many errors may be included in the six control parameters output to the bed controller 11 finally.

Therefore, as shown in FIG. 5B2, the generator 103 is configured to cause the first DRR image DI1 generated by virtually enlarging the range of the portion of the patient P shown in the DRR image DI, i.e., by extending the photography range in the radiation detector 30-1 (the FPD) corresponding to the DRR image DI, to include the portion of the patient P. More specifically, the generator 103 is configured to generate the first DRR image DI1 by extending the photography range to a range including all CT data (three-dimensional volume data) of the patient P acquired and output by the first image acquirer 101 when viewed from a direction of a plane on which the radiation detector 30-1 detects radiation (X-rays) radiated from the radiation source 20-1, passing through the body of the patient P, and arriving thereat, i.e., a direction (an angle) in (at) which the radiation detector 30-1 captures the X-ray fluoroscopic image PI. A state in which the photographing range in the DRR image DI shown in FIG. 5B1 is extended to the left side and the upper side is shown in FIG. 5B2. Thereby, as shown in FIG. 5B3, the generator 103 generates the first DRR image DI1 in which the entire head of the patient P is shown by extending the photography range in the DRR image DI shown in FIG. 5B1 to the left and upper sides. Thereby, the region of the portion of the patient P included in the X-ray fluoroscopic image PI shown in FIG. 5A is included in the first DRR image DI1 shown in FIG. 5B3 and it is possible to calculate an evaluation value (a degree of similarity) based on an evaluation function, i.e., the amount of misalignment of the patient P, with higher accuracy from pixel values of each of the X-ray fluoroscopic image PI shown in FIG. 5A and the first DRR image DI1 shown in FIG. 5B3.

(Sparse Search Method for CT Position)

Figure 6:
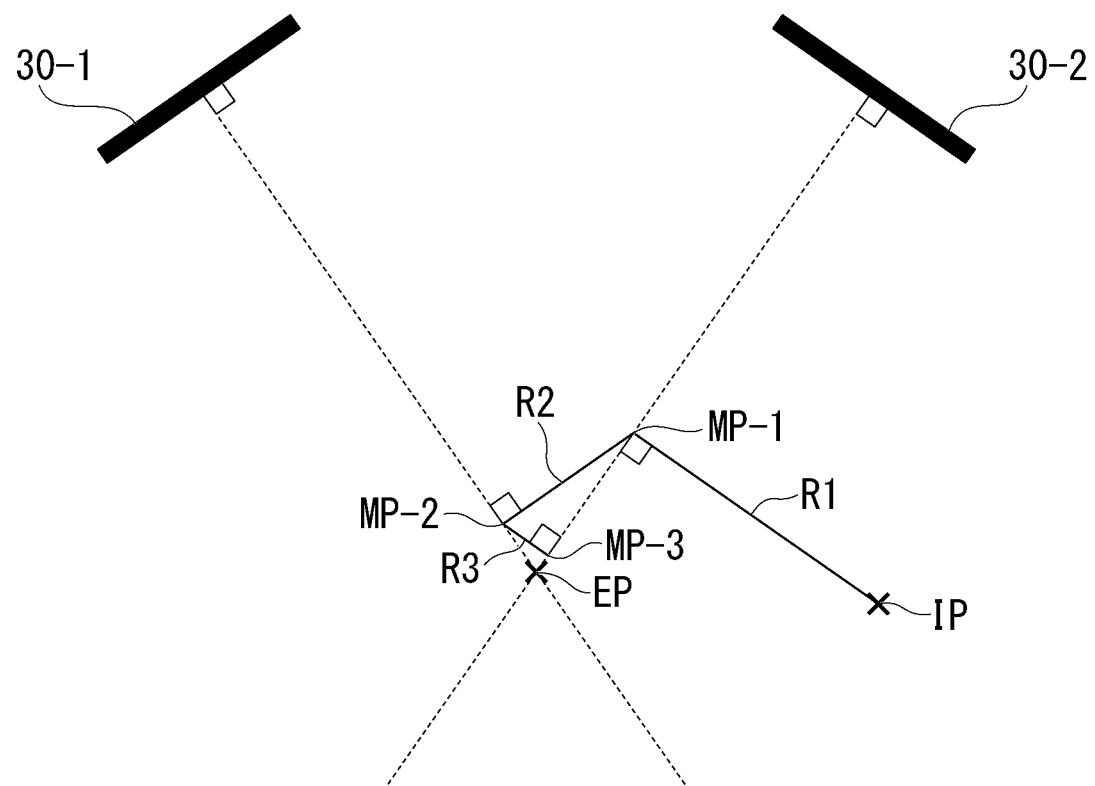
FIG. 6 is a diagram showing an operation of obtaining a suitable position using a reconstructed image generated by the medical image processing device of the first embodiment.

Next, a sparse search method for a CT position (a suitable position) in the first calculator 1041 will be described. FIG. 6 is a diagram showing an operation of obtaining a suitable position (CT position) using a reconstructed image (a first DRR image DI1) generated by the generator 103 provided in the medical image processing device 100 of the first embodiment. An example of a state until the amount of misalignment of the patient P, i.e., the CT position found in the sparse search, is within a prescribed range from the end position when the sparse search is performed three times from an initial position of the CT position is shown in FIG. 6.

First, when the current position is the initial position IP, the generator 103 generates the first DRR image DI1 corresponding to the radiation detector 30-2 and outputs the first DRR image DI1 to the first calculator 1041. More specifically, the generator 103 generates a first DRR image DI1 (for example, the first DRR image DI1 shown in FIG. 5B3) including CT data virtually arranged at an initial position IP within the three-dimensional space of the treatment room where the treatment system 1 is installed and representing a two-dimensional plane parallel to the plane on which the radiation detector 30-2 detects radiation (X-rays) and outputs the first DRR image DI1 to the first calculator 1041.

Thereby, the first calculator 1041 searches for a suitable position (CT position) in the current first DRR image while sequentially moving the CT position included in the first DRR image DI1 output by the generator 103 along the two-dimensional plane represented by the first DRR image DI1. More specifically, the first calculator 1041 searches for a CT position having the best output (the best degree of similarity) of the evaluation function obtained from pixel values of each of the current first DRR image DI1 and the X-ray fluoroscopic image PI corresponding to the radiation detector 30-2 while sequentially moving the CT position included in the current first DRR image DI1 by one pixel at a time. Here, vertical and horizontal lengths of each pixel included in the first DRR image DI1 in the three-dimensional space can be obtained in a simple geometric calculation process based on geometric information of the photography device in the treatment system 1. Thus, the first calculator 1041 converts the obtained vertical and horizontal lengths of each pixel in the three-dimensional space into vertical and horizontal lengths of each pixel arranged in a two-dimensional plane in the first DRR image DI1. The first calculator 1041 searches for a CT position where the output (the degree of similarity) of the evaluation function is the best while moving the CT position by one pixel at a time on the basis of the converted vertical and horizontal lengths. A state in which the CT position is moved along a search path R1 within the plane of the current first DRR image DI1 corresponding to the radiation detector 30-2 and the best CT position at present is found as an intermediate position MP-1 in the search is shown in FIG. 6. Although the search path R1 is represented by one straight line in FIG. 6, the first calculator 1041 causes the CT position to be moved along the two-dimensional plane represented by the first DRR image DI1 as described above. Thus, the search path R1 is a path along which the CT position is linearly moved in the vertical direction and the horizontal direction within the first DRR image DI1. The first calculator 1041 outputs information representing the intermediate position MP-1 found in the search to the generator 103.

Subsequently, the generator 103 generates the first DRR image DI1 corresponding to the radiation detector 30-1 on the basis of information representing the intermediate position MP-1 output by the first calculator 1041 and outputs the first DRR image DI1 to the first calculator 1041. More specifically, as in the case when the first DRR image DI1 corresponding to the radiation detector 30-2 is generated, the generator 103 generates a first DRR image DI1 including CT data virtually arranged at the intermediate position MP-1 within the three-dimensional space of the treatment room where the treatment system 1 is installed and representing a two-dimensional plane parallel to the plane on which the radiation detector 30-1 detects radiation (X-rays) and outputs the first DRR image DI1 to the first calculator 1041.

Thereby, as in the case when the intermediate position MP-1 is searched for, the first calculator 1041 searches for a suitable position (CT position) in the current first DRR image DI1 while sequentially moving the CT position included in the current first DRR image DI1 by one pixel at a time. However, here, the first calculator 1041 searches for a CT position where the output (the degree of similarity) of the evaluation function obtained from pixel values of each of the current first DRR image DI1 and the X-ray fluoroscopic image PI corresponding to the radiation detector 30-1 becomes best. A state in which the CT position is moved along a search path R2 within the plane of the current first DRR image DI1 corresponding to the radiation detector 30-1 and the best CT position at present is found as an intermediate position MP-2 in the search is shown in FIG. 6. Also, like the search path R1, the search path R2 represented by one straight line in FIG. 6 is also a path for linearly moving the CT position in the vertical direction and the horizontal direction within the current first DRR image DI1. The first calculator 1041 outputs information representing the intermediate position MP-2 found in the search to the generator 103.

Subsequently, similarly, the generator 103 generates the first DRR image DI1 corresponding to the radiation detector 30-2 including CT data virtually arranged at the intermediate position MP-2 on the basis of information representing the intermediate position MP-2 output by the first calculator 1041 and outputs the first DRR image DI1 to the first calculator 1041. Likewise, the first calculator 1041 also searches for a CT position where the output (the degree of similarity) of the evaluation function obtained from pixel values of each of the current first DRR image DI1 and the X-ray fluoroscopic image PI corresponding to the radiation detector 30-2 becomes best. A state in which the CT position is moved along a search path R3 within the plane of the current first DRR image DI1 corresponding to the radiation detector 30-2 and the best CT position at present is found as an intermediate position MP-3 in the search is shown in FIG. 6. Also, like the search path R1, the search path R3 shown in FIG. 6 is also a path for linearly moving the CT position in the vertical direction and the horizontal direction within the current first DRR image DI1 corresponding to the radiation detector 30-2.

Subsequently, likewise, the generator 103 iterates the generation of the first DRR image DI1 corresponding to one radiation detector 30 and the search for the best CT position at the present time by the first calculator 1041. Thereby, the CT position found in the sparse search in the first calculator 1041 is approximated to an end position EP, i.e., a final CT position.

As described above, the sparse search in the first calculator 1041 is a simple search for the CT position that is performed until the position of the patient P fixed on the treatment table 10 can be adjusted to some extent. Therefore, the first calculator 1041 ends the sparse search when the CT position found in the sparse search falls within a prescribed range from the end position EP, i.e., when the amount of misalignment of the patient P falls within a prescribed range. In FIG. 6, the sparse search is completed when the first calculator 1041 has found the CT position of the intermediate position MP-3 in the search. Subsequently, the calculation of the amount of misalignment of the patient P in the calculator 104 is transferred to the second calculator 1042. In this case, the first calculator 1041 outputs information representing the intermediate position MP-3 found in the search to the second calculator 1042 and ends the sparse search.

Here, the number of times the first calculator 1041 iterates the sparse search, i.e., the prescribed range of the amount of misalignment of the patient P for the first calculator 1041 to determine to end the sparse search, is determined according to a predetermined threshold value of the degree of similarity with respect to the output (the degree of similarity) of the evaluation function obtained from pixel values of each of the first DRR image DI1 and the X-ray fluoroscopic image PI. Also, the condition for the first calculator 1041 to determine that the amount of misalignment of the patient P is within the prescribed range may be another predetermined condition. For example, the first calculator 1041 may determine that the amount of misalignment of the patient P is within a prescribed range when the sparse search has been performed a predetermined number of times. Also, for example, the first calculator 1041 may determine that the amount of misalignment of the patient P is within the prescribed range when a distance associated with an image of the same lesion, bone, or the marker in the body of the patient P shown in the first DRR image DI1 and the X-ray fluoroscopic image PI is less than or equal to an actual distance capable of being represented in the X-ray fluoroscopic image PI by each X-ray detector arranged in the radiation detector 30 (the FPD), i.e., a so-called pixel pitch of each pixel constituting the X-ray fluoroscopic image PI. Also, for example, the first calculator 1041 may determine that the amount of misalignment of the patient P is within the prescribed range if the amount of movement of the CT position when the amount of misalignment of the patient P is calculated becomes less than or equal to a prescribed amount of movement, in other words, if a distance between a CT position found in a previous sparse search and a CT position found in a current sparse search is less than or equal to a prescribed distance. Also, for example, the first calculator 1041 may determine that the amount of misalignment of the patient P is within the prescribed range when a distance associated with an image of the same lesion, bone, or the marker in the body of the patient P shown in the first DRR image DI1 and the X-ray fluoroscopic image PI is less than or equal to a distance (for example, 0.5 [mm]) within a searchable range where the second calculator 1042 can continuously search for a CT position with the smallest amount of misalignment of the patient P, in other words, when a state in which the calculation of the amount of misalignment of the patient P can be transferred to the second calculator 1042 has been reached.

(Dense Search Method for CT Position)

Next, a dense search for the CT position (the suitable position) in the second calculator 1042 will be described. As described above, the second calculator 1042 performs a dense search based on the second DRR image DI2 and the X-ray fluoroscopic image PI, following the sparse search in the first calculator 1041. The dense search in the second calculator 1042 is similar to the search for the CT position in the conventional general treatment system. That is, in the dense search in the second calculator 1042, the final suitable position (CT position) is searched for without limiting the movement of the CT position within the two-dimensional plane as in the sparse search in the first calculator 1041. More specifically, the second calculator 1042 obtains the output (the degree of similarity) of the evaluation function from pixel values of each of the second DRR image DI2 and the X-ray fluoroscopic image PI corresponding to each radiation detector 30 at each CT position and performs a dense search for a CT position where the output (the degree of similarity) of the evaluation function becomes best while randomly moving a CT position in accordance with six parameters representing the amount of rotation and the amount of translation based on the three-dimensional coordinates within the treatment room. Also, the second calculator 1042 may perform a dense search for a CT position where the output (the degree of similarity) of the evaluation function becomes best while sequentially moving a CT position in accordance with six parameters representing the amount of rotation and the amount of translation based on the three-dimensional coordinates within the treatment room.

However, when the second calculator 1042 performs a dense search, the amount of misalignment of the patient P is within a prescribed range by the first calculator 1041. That is, a state in which the position of the patient P fixed on the treatment table 10 is adjusted to some extent is reached. Thus, the second calculator 1042 can perform a dense search for the final suitable position (CT position) in a state in which a movement range of the CT position included in the second DRR image DI2 is narrowed down on the basis of the CT position where the first calculator 1041 has completed the sparse search. For example, the second calculator 1042 can perform a dense search for the CT position by setting the movement range of the CT position as a prescribed range centered on the CT position found in the sparse search in the first calculator 1041.

The second calculator 1042 calculates six control parameters for moving the treatment table 10 on the basis of the final CT position found in the dense search and outputs the calculated six control parameters to the bed controller 11. Thereby, the bed controller 11 causes the treatment table 10 to be moved in accordance with the six control parameters output by the second calculator 1042.

As described above, the second calculator 1042 may be configured to allow the radiation treatment practitioner (the doctor or the like) using the treatment system 1 to confirm information of the final CT position by outputting the information to the display controller 60 before the six control parameters for moving the treatment table 10 are calculated on the basis of the final CT position found in the search. In this case, the display controller 60 generates a display DRR image DI corresponding to each radiation detector 30 on the basis of the second DRR image DI2 generated by the generator 103 and causes the display device 61 to display a confirmation display image in which the generated display DRR image DI corresponding to each radiation detector 30 is superimposed on a corresponding X-ray fluoroscopic image PI of the radiation detector 30 acquired by the second image acquirer 102. Further, the display controller 60 causes the display device 61 to display a state in which the final CT position found in the search in the second calculator 1042 is superimposed on the confirmation display image in which the display DRR image DI is superimposed on the corresponding X-ray fluoroscopic image PI. Also, the display DRR image DI is not generated by the display controller 60, but may be generated by the generator 103 on the basis of the final CT position found in the search in the second calculator 1042 and output to the display controller 60. In this case, the display controller 60 is configured so that the display DRR image DI generated by the generator 103 is superimposed on the corresponding X-ray fluoroscopic image PI and the final CT position is further superimposed thereon and a superimposition result is displayed on the display device 61.

Also, the second calculator 1042 may acquire information for adjusting the final CT position adjusted by the radiation treatment practitioner (the doctor or the like) on the basis of the display DRR image DI, the X-ray fluoroscopic image PI, and the final CT position displayed on the display device 61 output by the instruction receiver 80. In this case, the second calculator 1042 calculates six control parameters for moving the treatment table 10 by reflecting the information for adjusting the final CT position output by the instruction receiver 80 in the CT position found in the search and outputs the calculated six control parameters to the bed controller 11. Thereby, the bed controller 11 causes the treatment table 10 to be moved in accordance with the six control parameters in which the CT position adjusted by the radiation treatment practitioner (the doctor or the like) has been reflected output by the second calculator 1042.

As described above, the medical image processing device 100 of the first embodiment performs a position determination process for moving the patient P fixed on the treatment table 10 to a position suitable for radiation treatment by searching for the final CT position (the suitable position) in the two-step search including the sparse search in the first calculator 1041 and the dense search in the second calculator 1042. Here, the first DRR image DI1 used in the sparse search in the first calculator 1041 is wider than the photography range of the radiation detector 30 (the FPD) in terms of a plane, but a range in which the CT position is moved is a range of a two-dimensional plane. Also, the dense search in the second calculator 1042 is performed only once in a state in which the range in which the CT position is moved in the second DRR image DI2 is narrowed down. Thus, the treatment system 1 having the medical device including the medical image processing device 100 of the first embodiment can perform a process of determining a position of the patient P with high accuracy in a state in which the calculation cost, which is the calculation load for searching the CT position, is limited even if there is a large difference between the portion in the body of the patient P shown in the DRR image DI and the portion in the body of the patient P shown in the X-ray fluoroscopic image captured by the photography device.

Also, the case in which each of the first calculator 1041 and the second calculator 1042 provided in the calculator 104 adjusts a CT position to three-dimensional coordinates of the treatment room where the photography device including the set of the radiation source 20 and the radiation detector 30 is installed by moving the CT position included in the DRR image DI1 in the medical image processing device 100 when the process of determining the position of the patient P is performed as described above has been described. However, in actual radiation treatment, the treatment beam B is radiated to the patient P from a direction predetermined in the stage of treatment planning or the like. Therefore, the final six control parameters output by the medical image processing device 100 to the bed controller 11 are control parameters obtained by performing an inverse operation from the final CT position found in the search so that the patient P fixed on the treatment table 10 is directed in a predetermined suitable direction in which the treatment beam B is radiated to perform radiation treatment. In other words, the control parameters are control parameters for changing the direction of the patient P fixed on the treatment table 10 so that each radiation detector 30 can capture the X-ray fluoroscopic image PI which is the same as the pre-planned DRR image DI.

Thus, in the treatment system 1, after the position determination process of the medical image processing device 100 is completed and the treatment table 10 is moved, the photography device may capture the X-ray fluoroscopic image PI again and reconfirm the direction of the patient P. The X-ray fluoroscopic image PI captured in this case becomes an image of the patient P captured from a predetermined suitable direction. The treatment system 1 may be configured so that the treatment beam B is radiated to the lesion in the body of the patient P after the display DRR image DI, the X-ray fluoroscopic image PI, which has been captured again, and the final CT position are superimposed and displayed on the display device 61 and the radiation treatment practitioner (the doctor or the like) finally makes confirmation (determination).

Also, as a result of the final confirmation (determination) by the radiation treatment practitioner (the doctor or the like), when the treatment beam B is not radiated, the medical image processing device 100 may automatically perform the process of determining the position of the patient P again or the radiation treatment practitioner (the doctor or the like) may manually adjust the position of patient P. Here, when the medical image processing device 100 automatically performs the process of determining the position of the patient P again, the first calculator 1041 does not perform the sparse search, but the second calculator 1042 may only perform the dense search. Also, if the radiation treatment practitioner (the doctor or the like) manually adjusts the position of the patient P, the position of the patient P may be adjusted within the two-dimensional plane using information when the vertical and horizontal lengths in the three-dimensional space have been converted into vertical and horizontal lengths within a two-dimensional plane so that a CT position is moved in the sparse search in the first calculator 1041.

As described above, the medical image processing device 100 includes the first image acquirer 101 configured to acquire a three-dimensional volume data image (a CT image CI) of the patient P; the second image acquirer 102 configured to acquire an X-ray fluoroscopic image PI according to radiation (X-rays) with which the patient P is irradiated at a time point different from a time point of acquisition of the CT image CI from a photography device that detects radiated radiation (X-rays) with the radiation detector 30 and performs an imaging process (a process of forming the X-ray fluoroscopic image PI); the generator 103 configured to generate a reconstructed image (a DRR image DI) obtained by reproducing the X-ray fluoroscopic image PI from the CT image CI virtually arranged in a three-dimensional space on the basis of an installation position of the radiation detector 30 in the three-dimensional space; and the calculator 104 configured to obtain a suitable position on the CT image CI in the three-dimensional space on the basis of a degree of similarity (an evaluation value) between the X-ray fluoroscopic image PI and the DRR image DI, wherein the generator 103 generates the DRR image DI for use in the calculator 104 so that a range larger than a range corresponding to the X-ray fluoroscopic image PI is provided.

Also, as described above, in the medical image processing device 100, the DRR image DI generated to provide the range larger than the range corresponding to the X-ray fluoroscopic image PI among DRR images DI may be generated to include a target portion of the patient P.

Also, as described above, the generator 103 may generate a first reconstructed image (a first DRR image DI1) of the range larger than the range corresponding to the X-ray fluoroscopic image PI among the DRR images DI and a second reconstructed image (a second DRR image DI2) other than the first DRR image DI1 among the DRR images DI and the calculator 104 may include the first calculator 1041 configured to obtain a first position where the degree of similarity between the target portion included in the first reconstructed image and the target portion included in the second fluoroscopic image is higher by virtually moving the first DRR image DI1 parallel with respect to the X-ray fluoroscopic image PI and the second calculator 1042 configured to obtain a second position where the degree of similarity between the target portion included in the second DRR image DI2 and the target portion included in the X-ray fluoroscopic image PI is higher by causing the second DRR image DI2 to be virtually subjected to parallel and rotation movements with respect to the X-ray fluoroscopic image PI on the basis of the first position obtained by the first calculator 1041 and output the second position as the suitable position that is final.

Also, as described above, the generator 103 may generate the first DRR image DI1 corresponding to the radiation detector 30 that detects the radiation radiated from at least a first direction and the first DRR image DI1 corresponding to the radiation detector 30 that detects the radiation radiated from a second direction different from the first direction with respect to the patient and generate the second DRR image DI2 including information indicating the direction in which each radiation detector 30 detects the radiation.

Also, as described above, the first calculator 1041 may obtain at least the first position using the first DRR image DI1 corresponding to one radiation detector 30 that detects the radiation radiated from one of the first direction and the second direction.

Also, as described above, the first calculator 1041 may iterate a process of obtaining the first position using the first DRR image DI1 corresponding to the radiation detector 30 that detects the radiation radiated from one of the first direction and the second direction and a process of obtaining the first position where the degree of similarity between the target portion included in the first DRR image DI1 and the target portion included in the X-ray fluoroscopic image Pt is higher using the first DRR image DI1 corresponding to the radiation detector 30 that detects the radiation radiated from the other direction on the basis of the first position until the degree of similarity between the target portion included in the first DRR image DI1 and the target portion included in the X-ray fluoroscopic image PI is within a prescribed range, and the second calculator 1042 may obtain the second position on the basis of the first position within the prescribed range.

Also, as described above, the generator 103 may generate the first reconstructed image corresponding to the other radiation detector 30 after the first calculator 1041 obtains the first position corresponding to one radiation detector 30.

Also, as described above, the medical image processing device 100 may further include the display controller 60 configured to cause the display device 61 to display the CT image CI and the X-ray fluoroscopic image PI and cause the display device 61 to further display information of the suitable position; and the instruction receiver 80 configured to receive an instruction for moving the suitable position within the three-dimensional space of the CT image CI.

Also, as described above, the medical device may include the medical image processing device 100 and a photography device including the two radiation detectors 30 configured to detect radiation (X-rays) radiated from different directions to the patient P.

Also, as described above, the treatment system 1 may include a medical device, a treatment beam irradiation gate 40 configured to irradiate a treatment target portion of the patient P with the treatment beam B; the treatment beam irradiation controller 41 configured to control the irradiation with the treatment beam B; and the bed controller 11 configured to cause a position of the treatment table 10 on which the patient P is fixed to be moved so that the position is adjusted to a suitable position obtained in the medical device.

Also, the medical image processing device 100 may be a device including a processor such as a CPU and a GPU and a storage device such as a ROM, a RAM, an HDD, or a flash memory, wherein the storage device stores a program for causing the processor to function as the first image acquirer 101 configured to acquire a three-dimensional volume data image (a CT image CI) of a patient P; the second image acquirer 102 configured to acquire an X-ray fluoroscopic image PI according to radiation (X-rays) with which the patient P is irradiated at a time point different from a time point of acquisition of the CT image CI from a photography device that detects radiated radiation (X-rays) with the radiation detector 30 and performs an imaging process (a process of forming the X-ray fluoroscopic image PI); the generator 103 configured to generate a reconstructed image (a DRR image DT) obtained by reproducing the X-ray fluoroscopic image PI from the CT image CI virtually arranged in a three-dimensional space on the basis of an installation position of the radiation detector 30 in the three-dimensional space; and the calculator 104 configured to obtain a suitable position on the CT image CI in the three-dimensional space on the basis of the degree of similarity (an evaluation value) between the X-ray fluoroscopic image PI and the DRR image DI, wherein the generator 103 generates the DRR image DI for use in the calculator 104 so that a range larger than a range corresponding to the X-ray fluoroscopic image PI is provided.

Second Embodiment

Hereinafter, a second embodiment will be described. Also, a configuration of a treatment system including a medical image processing device of the second embodiment is a configuration in which the medical image processing device 100 in the configuration of the treatment system 1 including the medical image processing device 100 of the first embodiment shown in FIG. 1 is replaced with the medical image processing device of the second embodiment (hereinafter referred to as a "medical image processing device 200"). In the following description, the treatment system including the medical image processing device 200 is referred to as a "treatment system 2."

Also, in the following description, components of the treatment system 2 including the medical image processing device 200 similar to the components of the treatment system 1 including the medical image processing device 100 of the first embodiment are denoted by the same reference signs and detailed description thereof will be omitted. In the following description, only a configuration, an operation, and a process of the medical image processing device 200, which is a component different from the medical image processing device 100 of the first embodiment, will be described.

The medical image processing device 200 performs a position determination process of aligning a current position of a patient P with a predetermined position like the medical image processing device 100 of the first embodiment. That is, like the medical image processing device 100 of the first embodiment, the medical image processing device 200 also obtains the amount of movement of the treatment table 10 for causing the current position of the patient P fixed on the treatment table 10 to be moved to a predetermined suitable position in a two-step search process including a sparse search and a dense search.

Figure 7:
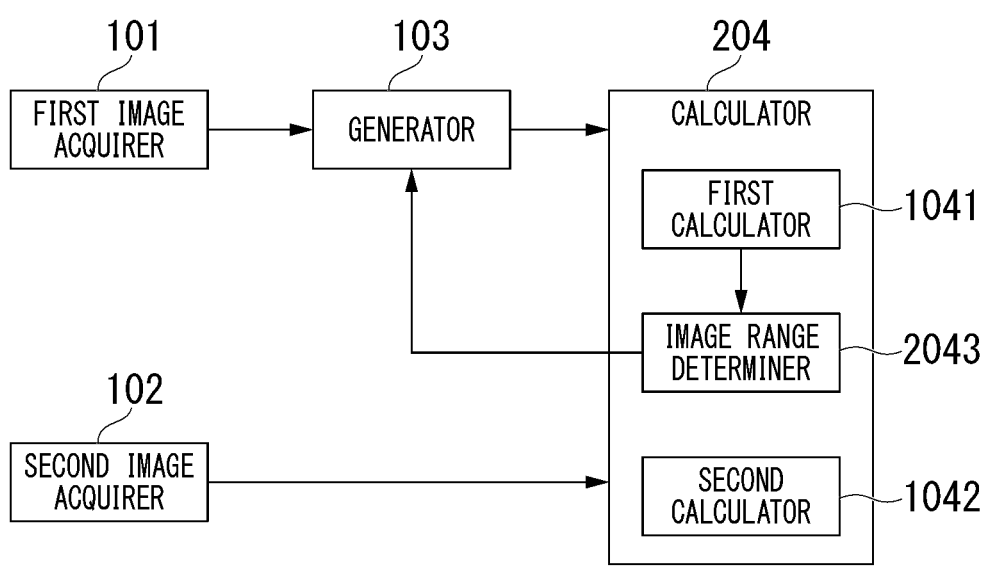
FIG. 7 is a block diagram showing a schematic configuration of a medical image processing device of a second embodiment.

Hereinafter, a configuration of the medical image processing device 200 constituting the treatment system 2 will be described. FIG. 7 is a block diagram showing a schematic configuration of the medical image processing device 200 of the second embodiment. The medical image processing device 200 shown in FIG. 7 includes a first image acquirer 101, a second image acquirer 102, a generator 103, and a calculator 204. Also, the calculator 204 includes a first calculator 1041, a second calculator 1042, and an image range determiner 2043.

The medical image processing device 200 has a configuration in which the calculator 104 constituting the medical image processing device 100 of the first embodiment is replaced with the calculator 204. The calculator 204 has a configuration in which the image range determiner 2043 is added to the calculator 104 constituting the medical image processing device 100 of the first embodiment. Also, the other components provided in the medical image processing device 200 are the same as those provided in the medical image processing device 100 of the first embodiment. Therefore, in the following description, components of the medical image processing device 200 similar to the components provided in the medical image processing device 100 of the first embodiment are denoted by the same reference signs and detailed description of the similar components will be omitted. In the following description, only the components different from those of the medical image processing device 100 of the first embodiment will be described.

In the medical image processing device 200, the first calculator 1041 provided in the calculator 204 outputs information about a CT position found in the sparse search using a current first DRR image DI to the image range determiner 2043 instead of the generator 103.

The image range determiner 2043 determines a photography range of a first DRR image DI1 used by the first calculator 1041 in the next sparse search on the basis of the information about the CT position output by the first calculator 1041. The image range determiner 2043 outputs information about the determined photography range of the first DRR image DI1 and the information about the CT position output by the first calculator 1041 to the generator 103. Thereby, the generator 103 generates a new first DRR image DI1 to be used in the next sparse search in the first calculator 1041 according to a size based on the information about the photography range of the first DRR image DI1 on the basis of the CT position in the current first DRR image DI1 output by the image range determiner 2043 and outputs the new first DRR image DI1, which has been generated, to the first calculator 1041.

According to the above configuration, the medical image processing device 200 can perform a process of determining a position of the patient P with high accuracy in a state in which the calculation cost when the first calculator 1041 performs the sparse search for the CT position is less than the calculation cost in the medical image processing device 100 of the first embodiment.

Here, a method of determining the photography range of the first DRR image DI1 in the image range determiner 2043 will be described. Also, in the following description, a method of determining the photography range of the first DRR image DI1 in the image range determiner 2043 will be described with reference to an example of an operation of obtaining a CT position using the first DRR image DI1 shown in FIG. 6.

The photography range of the first DRR image DI1 for use in the sparse search in the first calculator 1041 is wider than a photography range of a radiation detector 30 (an FPD) when considered in a plane. However, when the CT position found in the sparse search in the first calculator 1041 is close to an end position, i.e., a final CT position in the sparse search, it is thought that there will be no problem even if the range of the CT position to be moved by the first calculator 1041 in the sparse search is reduced. For example, when the sparse search in the first calculator 1041 is approaching the final stage and the distance between the CT position found in the sparse search and the final CT position in the sparse search is a distance within the photography range of the radiation detector 30 (the FPD), the photography range of the first DRR image DI1 can be set to the photography range of the radiation detector 30 (the FPD) or less. Thus, the image range determiner 2043 reduces the photography range of the first DRR image DI1 used by the first calculator 1041 in the next sparse search on the basis of information about the CT position output by the first calculator 1041.

More specifically, for example, in an example of the operation of obtaining the CT position using the first DRR image DI1 shown in FIG. 6, a range in which the CT position is moved within the plane of the first DRR image DI1 in the first sparse search is a range larger than the photography range of the radiation detector 30-2 (the FPD) along a search path R1. On the other hand, for example, in the example of the operation shown in FIG. 6, a range in which the CT position is moved in the plane of the first DRR image DI1 in the second sparse search is a range along the search path R2 and is smaller than the photography range of the radiation detector 30-1 (the FPD). Further, for example, in an example of the operation shown in FIG. 6, a range in which the CT position is moved in the plane of the first DRR image DI1 in the third sparse search is a range along a search path R3 and is smaller than the photography range of the radiation detector 30-2 (the FPD).

Therefore, the image range determiner 2043 predicts a distance of movement of the CT position in the next sparse search on the basis of a distance of movement of the CT position by the first calculator 1041 in the current sparse search and determines the photography range of the first DRR image DI1 for use in the first calculator 1041 in the next sparse search. For example, in an example of the operation shown in FIG. 6, a range of movement of the CT position within the plane of the first DRR image DI1 in the third sparse search is considered to be smaller than the photography range of the radiation detector 30-2 (the FPD) at a higher probability according to the first and second sparse searches. Thus, the image range determiner 2043 determines the photography range of the first DRR image DI1 for use in the third sparse search as, for example, a range which is the same as the photography range of the radiation detector 30-2 (the FPD). Thereby, the range of movement of the CT position by the first calculator 1041 in the third sparse search becomes the photography range of the radiation detector 30-2 (the FPD) and it is possible to avoid an increase in the calculation cost in the generator 103 when the first DRR image DI1 is generated more than necessary or the calculation cost of the sparse search in the first calculator 1041.

Also, as described above, for example, in the example of the operation shown in FIG. 6, the range in which the CT position is moved within the plane of the first DRR image DI1 in the second sparse search is also considered to be smaller than the photography range of the radiation detector 30-1 (the FPD). However, in the stage where the second sparse search is performed, only the first sparse search is completed and the probability at which the range of movement of the CT position within the plane of the first DRR image DI1 is considered to be smaller than the photography range of the radiation detector 30-1 (the FPD) is considered to be lower than that in the third sparse search. If the CT position with the smallest amount of misalignment of the patient P is a CT position beyond the photography range of the first DRR image DI1, the CT position in the second sparse search becomes the CT position at the end of the first DRR image DI1 and an increase in the number of times the first calculator 1041 iterates the sparse search thereafter is also considered. Thus, when a range in which the CT position is moved at a higher probability is smaller than the photography range of the radiation detector 30 (the FPD), the image range determiner 2043 is configured to reduce the photography range of the first DRR image DI1 for use in the first calculator 1041 in the next sparse search.

As described above, like the medical image processing device 100 of the first embodiment, the medical image processing device 200 of the second embodiment also performs a position determination process for moving the patient P fixed on the treatment table 10 to a suitable position for radiation treatment by searching for a final CT position (a suitable position) in a two-step search process including the sparse search in the first calculator 1041 and the dense search in the second calculator 1042. Further, in the medical image processing device 200 of the second embodiment, the image range determiner 2043 reduces the photography range of the first DRR image DI1 for use in the sparse search in the first calculator 1041. Thereby, the medical image processing device 200 of the second embodiment can perform a process of determining the position of the patient P with high accuracy in a state in which the calculation cost at the time of the sparse search in the first calculator 1041 is lower than the medical image processing device 100 of the first embodiment.

As described above, in the medical image processing device 200, the calculator 204 may further include the image range determiner 2043 configured to determine a range of the first DRR image DI1 which is subsequently generated on the basis of the amount of movement for causing the first reconstructed image (the first DRR image DI1I) to be virtually moved parallel with respect to the second fluoroscopic image (the X-ray fluoroscopic image) when the first position is obtained.

As described above, the medical image processing device of each embodiment, a position determination process for moving the patient fixed on the treatment table to a predetermined position so that the patient is irradiated with a treatment beam in radiation treatment is performed by searching for a suitable position in a two-step search process including a sparse search in the first calculator and a dense search in the second calculator. Thereby, the treatment system including the medical device including the medical image processing device of each embodiment can perform a process of determining the position of the patient with high accuracy while the calculation cost for searching for a suitable position is limited. In the treatment system including the medical device including the medical image processing device of each embodiment, it is possible to safely perform radiation treatment for irradiating the lesion with a treatment beam at an appropriate timing.

A medical image processing program for use in the medical image processing device described in the above-described embodiment is a medical image processing program for causing a computer to function as a medical image processing device including: a first image acquirer configured to acquire a first fluoroscopic image of a patient; a second image acquirer configured to acquire a second fluoroscopic image according to radiation with which the patient is irradiated at a time point different from a time point of acquisition of the first fluoroscopic image from a photography device that detects radiated radiation with a detector and performs an imaging process; a generator configured to generate a reconstructed image obtained by reproducing the second fluoroscopic image from the first fluoroscopic image virtually arranged in a three-dimensional space on the basis of an installation position of the detector in the three-dimensional space; and a calculator configured to obtain a suitable position on the first fluoroscopic image in the three-dimensional space on the basis of the degree of similarity between the second fluoroscopic image and the reconstructed image, wherein the generator generates the reconstructed image which is for use in the calculator and has a range larger than a range corresponding to the second fluoroscopic image.

According to at least one embodiment described above, there are provided a first image acquirer (101) configured to acquire a three-dimensional volume data image (a CT image) of a patient P; a second image acquirer (102) configured to acquire an X-ray fluoroscopic image according to radiation (X-rays) with which the patient P is irradiated at a time point different from a time point of acquisition of the CT image from a photography device that detects radiated radiation (X-rays) with a radiation detector (30) and performs an imaging process (a process of forming the X-ray fluoroscopic image); a generator (103) configured to generate a reconstructed image (a DRR image) obtained by reproducing the X-ray fluoroscopic image from the CT image virtually arranged in a three-dimensional space on the basis of an installation position of the radiation detector (30) in the three-dimensional space; and a calculator (104) configured to obtain a suitable position on the CT image in the three-dimensional space on the basis of the degree of similarity (an evaluation value) between the X-ray fluoroscopic image and the DRR image, wherein the generator (103) generates at least some of DRR images which is for use in the calculator (104) and has a range larger than a range corresponding to the X-ray fluoroscopic image. Therefore, it is possible to align the position of a patient with high accuracy.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing device comprising:
a first image acquirer configured to acquire a computed tomography (CT) image of a patient;
a second image acquirer configured to acquire an X-ray fluoroscopic image having a first photography range according to radiation with which the patient is irradiated at a time point different from a time point of acquisition of the CT image from a photography device that detects radiated radiation with a detector having the first photography range and performs an imaging process;

a generator configured to generate a digitally reconstructed radiograph (DRR) image obtained by reproducing the X-ray fluoroscopic image from data of the CT image virtually arranged in a three-dimensional space on the basis of an installation position of the detector in the three-dimensional space; and a calculator configured to obtain a suitable position on the CT image in the three-dimensional space on the basis of a degree of similarity between the X-ray fluoroscopic image and the DRR image, wherein the generator generates the DRR image which is for use in the calculator and has a second photography range, along a two-dimensional plane parallel to a plane on which the detector detects radiation, virtually enlarged to be larger than the first photography range corresponding to the X-ray fluoroscopic image, the DRR image including a target portion of the patient, wherein the generator generates a first DRR image having the second photography range larger than the first photography range and a second DRR image having the first photography range corresponding to the X-ray fluoroscopic image, wherein the calculator includes a first calculator configured to obtain a first position where a degree of similarity between the target portion included in the first DRR image and the target portion included in the X-ray fluoroscopic image is higher by virtually moving the first DRR image parallel with respect to the X-ray fluoroscopic image, and a second calculator configured to obtain the suitable position which is a second position where a degree of similarity between the target portion included in the second DRR image and the target portion included in the X-ray fluoroscopic image is higher by causing the CT image to be virtually subjected to parallel and rotation movements on the basis of the first position, wherein the first position is a position of the CT image in the three-dimensional space on the basis of a position of the first DRR image in the three-dimensional space, and the second position is a position of the CT image in the three-dimensional space on the basis of a position of the second DRR image in the three-dimensional space and wherein the generator is configured to generate the DRR image which is for use in the calculator and has the second photography range virtually enlarged by including all data in the CT image of the patient acquired and output by the first image acquirer when viewed from a direction of a plane on which the detector of the photography device detects the radiated radiation.

2. The medical image processing device according to claim 1, wherein the calculator outputs the second position as the suitable position that is final.

3. The medical image processing device according to claim 2, wherein the calculator further includes an image range determiner configured to determine a range of the first DRR image, which is subsequently generated, on the basis of an amount of movement for virtually moving the first DRR image parallel with respect to the second DRR image when the first position is obtained.

4. The medical image processing device according to claim 2, wherein the generator generates the first DRR image corresponding to the detector that detects the radiation radiated from at least a first direction and the first DRR image corresponding to the detector that detects the radiation radiated from a second direction different from the first direction with respect to the patient and generates the second DRR image including information indicating the direction in which the detector detects the radiation.

5. The medical image processing device according to claim 4, wherein the first calculator obtains at least the first position using the first DRR image corresponding to one detector that detects the radiation radiated from one of the first direction and the second direction.

6. The medical image processing device according to claim 5, wherein the first calculator iterates a process of obtaining the first position using the first DRR image corresponding to the one detector that detects the radiation radiated from one of the first direction and the second direction and a process of obtaining the first position where a degree of similarity between the target portion included in the first DRR image and the target portion included in the X-ray fluoroscopic image is higher using the first DRR image corresponding to a second detector that detects the radiation radiated from the other direction on the basis of the first position until the degree of similarity between the target portion included in the first DRR image and the target portion included in the X-ray fluoroscopic image is within a prescribed range, and wherein the second calculator obtains the second position on the basis of the first position within the prescribed range.

7. The medical image processing device according to claim 6, wherein the generator generates the first DRR image corresponding to the second detector after the first calculator obtains the first position corresponding to one detector.

8. The medical image processing device according to claim 1, further comprising:

a display controller configured to cause a display device to display the CT image and the X-ray fluoroscopic image and cause the display device to further display information of the suitable position; and a receiver configured to receive an instruction for moving the suitable position within the three-dimensional space of the CT image.

9. A computer-readable non-transitory storage medium storing a medical image processing program for causing a computer to function as a medical image processing device including:

a first image acquirer configured to acquire a computed tomography (CT) image of a patient;

a second image acquirer configured to acquire an X-ray fluoroscopic image having a first photography range according to radiation with which the patient is irradiated at a time point different from a time point of acquisition of the CT image from a photography device that detects radiated radiation with a detector having the first photography range and performs an imaging process;

a generator configured to generate a digitally reconstructed radiograph (DRR) image obtained by reproducing the X-ray fluoroscopic image from data of the CT image virtually arranged in a three-dimensional space on the basis of an installation position of the detector in the three-dimensional space; and a calculator configured to obtain a suitable position on the CT image in the three-dimensional space on the basis of a degree of similarity between the X-ray fluoroscopic image and the DRR reconstructed image, wherein the generator generates the DRR reconstructed image which is for use in the calculator and has a second photography range, along a two-dimensional plane parallel to a plane on which the detector detects radiation, virtually enlarged to be larger than the first photography range corresponding to the X-ray fluoroscopic image, the DRR image including a target portion of the patient, wherein the generator generates a first DRR image having the second photography range larger than the first photography range and a second DRR image having the first photography range corresponding to the X-ray fluoroscopic image, wherein the calculator includes a first calculator configured to obtain a first position where a degree of similarity between the target portion included in the first DRR image and the target portion included in the X-ray fluoroscopic image is higher by virtually moving the first DRR image parallel with respect to the X-ray fluoroscopic image, and a second calculator configured to obtain the suitable position which is a second position where a degree of similarity between the target portion included in the second DRR image and the target portion included in the X-ray fluoroscopic image is higher by causing the CT image to be virtually subjected to parallel and rotation movements on the basis of the first position, wherein the first position is a position of the CT image in the three-dimensional space on the basis of a position of the first DRR image in the three-dimensional space, and the second position is a position of the CT image in the three-dimensional space on the basis of a position of the second DRR image in the three-dimensional space, and wherein the generator is configured to generate the DRR image which is for use in the calculator and has the second photography range virtually enlarged by including all data in the CT image of the patient acquired and output by the first image acquirer when viewed from a direction of a plane on which the detector of the photography device detects the radiated radiation.

10. A medical device comprising:

the medical image processing device according to claim 1; and the photography device including two detectors configured to detect the radiation with which the patient has been irradiated from different directions.

11. A treatment system comprising:

the medical device according to claim 10;

an irradiator configured to irradiate a treatment target portion of the patient with a treatment beam;

an irradiation controller configured to control irradiation with the treatment beam; and a bed controller configured to cause a position of a bed on which the patient is fixed to be moved in association with the suitable position obtained in the medical device.

* * * * *